(12) United States Patent
Jacobsen et al.

(10) Patent No.: US 10,980,757 B2
(45) Date of Patent: Apr. 20, 2021

(54) READY-TO-USE TRANEXAMIC ACID INTRAVENOUS SOLUTION

(71) Applicant: RTU Pharma SA, Liege (BE)

(72) Inventors: Thomas Jacobsen, Leuven (BE); Eric Dubois, Brussels (BE)

(73) Assignee: RTU Pharma SA, Liege (BE)

( * ) Notice: Subject to any disclaimer, the term of this patent is extended or adjusted under 35 U.S.C. 154(b) by 222 days.

(21) Appl. No.: 16/392,865

(22) Filed: Apr. 24, 2019

(65) Prior Publication Data

US 2020/0078326 A1   Mar. 12, 2020

Related U.S. Application Data

(60) Provisional application No. 62/727,939, filed on Sep. 6, 2018.

(51) Int. Cl.
| | |
|---|---|
| *A61K 31/19* | (2006.01) |
| *A61P 7/04* | (2006.01) |
| *A61K 31/196* | (2006.01) |
| *A61K 9/00* | (2006.01) |

(52) U.S. Cl.
CPC .......... *A61K 31/196* (2013.01); *A61K 9/0019* (2013.01); *A61P 7/04* (2018.01)

(58) Field of Classification Search
CPC .................................. A61K 31/19; A61P 7/04
USPC ....................................................... 514/567
See application file for complete search history.

(56) References Cited

U.S. PATENT DOCUMENTS

| | | | |
|---|---|---|---|
| 3,268,405 A | 8/1966 | Nagasawa et al. | |
| 3,639,626 A | 2/1972 | Nagasawa et al. | |
| 3,950,405 A | 4/1976 | Okano et al. | |
| 4,600,582 A | 7/1986 | Stevens et al. | |
| 4,600,583 A | 7/1986 | Stevens et al. | |
| 6,162,242 A | 12/2000 | Peyman | |
| 6,622,729 B1 | 9/2003 | Peyman | |
| 7,235,530 B2 | 6/2007 | Blair et al. | |
| 8,173,627 B2 | 5/2012 | Yoo | |
| 8,188,045 B2 | 5/2012 | Blair et al. | |
| 9,168,216 B2 | 10/2015 | Gavin et al. | |
| 9,504,736 B2 | 11/2016 | Schmid-Schonbein et al. | |
| 9,603,965 B2 | 3/2017 | Bordoloi et al. | |
| 9,679,115 B2 | 6/2017 | Frey | |
| 9,775,821 B2 | 10/2017 | Hallam et al. | |
| 2011/0059894 A1 | 3/2011 | Rojkjaer et al. | |
| 2016/0206580 A1* | 7/2016 | Los | A61K 9/0014 |
| 2018/0000765 A1 | 1/2018 | Hallam et al. | |

FOREIGN PATENT DOCUMENTS

| | | |
|---|---|---|
| CN | 1965818 A | 5/2007 |
| CN | 103565743 A | 2/2014 |
| CN | 106109401 A | 11/2016 |
| EP | 0746334 A1 | 12/1996 |
| EP | 0803255 A1 | 10/1997 |
| WO | 9220361 | 11/1992 |
| WO | 2017007917 A1 | 1/2017 |

OTHER PUBLICATIONS

McCluskey et al., Stability of Tranexamic Acid in 0.9% Sodium Chloride, Stored in Type 1 Glass Vials and Ethylene/Propylene Copolymer Plastic Containers, International Journal of Pharmaceutical Compounding (2014), 8(5), 432-437, 7pgs.
PDR (Physician's Desk Reference), Tranexamic Acid (Cyklokapron (R)), Tablets and Injection (1996), 1950-1951, 3pgs.
Senghore, et al., The effect of tranexamic acid (cyclokapron) on blood loss after third molar extraction under a day case general anaesthetic, effect of different doses of tranexamic acid on postoperative blood loss in single knee arthroplasty, British Dental Journal (1999), 186(12), 634-636, 3pgs.
Yanartas, et al., The effects of tranexamic acid and 6% hydroxyethyl starch (HES) solution (130/0.4) on postoperative bleeding in coronary artery bypass graft (CABG) surgery, International Journal of Clinical and Experimental Medicine (2015), 8(4), 5959-5971, 13pgs.
Dunn, et al., Tranexamic Acid—A Review of its Use in Surgery and Other Indications, Drugs 1999 (June); 57(6); 1005-1032, 28pgs.
Liu, et al., Effect of different doses of tranexamic acid on postoperative blood loss in single knee arthroplasty, Qingdao Daxue Yixueyuan Xuebao (2015), 51(2), 163-165, 168, 4pgs.
Maged, et al., A randomized placebo-controlled trial of preoperative tranexamic acid among women undergoing elective cesarean delivery, International Journal of Gynecology & Obstetrics (2015), 131(3), 265-268, 4pgs.
Tengborn, et al., Tranexamic acid—an old drug still going strong and making a revival (2015) Thrombosis research 135 (2): 231-42, 11pgs.
Topsoee, et al., Anti-hemorrhagic effect of prophylactic tranexamic acid in benign hysterectomy—a double-blinded randomized placebo-controlled trial; American Journal of Obstetrics and Gynecology (2016), 215(1), 72.e1-72.e8, 8pgs.
Poeran, et al., Tranexamic acid use and postoperative outcomes in patients undergoing total hip or knee arthroplast in the United States: retrospective analysis of effectiveness and safety, British Medical Journal (2014), 349(7971), g4829/1-g4829/10, 10pgs.
Sentürk, et al., Tranexamic acid for cesarean section: a double-blind, placebo-controlled, randomized clinical trial, Archives of Gynecology and Obstetrics (2013), 287(4), 641-645, 5pgs.
Wang, et al., Efficacy and safety of tranexamic acid on reducing blood loss in bilateral total knee arthroplasty, Zhongguo Zuzhi Gongcheng Yanjiu (2015), 19(22), 3451-3456, 6pgs.
Yamamoto, et al., Clinical use of the trans form of 4-aminomethylcyclohexane-1-carboxylic acid on several skin diseases, Keio Journal of Medicine (1965), 14(3), 99-106, 8pgs.
Center for Drug Evaluation and Research, et al., Guidance for Industry for the Submission Documentation for Sterilization Process Validation in Applications for Human and Veterinary Drug Products, Nov. 1994, 23pgs.

\* cited by examiner

*Primary Examiner* — Raymond J Henley, III (74) *Attorney, Agent, or Firm* — Green, Griffith & Borg-Breen LLP

(57) ABSTRACT

Ready-to-use, stable aqueous intravenous tranexamic acid compositions are provided.

24 Claims, 1 Drawing Sheet

1

A    B

C    D

READY-TO-USE TRANEXAMIC ACID INTRAVENOUS SOLUTION

CROSS-REFERENCE TO RELATED APPLICATIONS

This application claims the benefit of U.S. Provisional Patent Application No. 62/727,939, which was filed on Sep. 6, 2018, the disclosure of which is incorporated by reference in its entirety herein.

DESCRIPTION OF THE RELATED ART

Tranexamic acid, trans-4-(aminomethyl)cyclohexanecarboxylic acid, is an antifibrinolytic agent. It produces an antifibrinolytic effect by competitively inhibiting the activation of plasminogen to plasmin. It is also a weak non-competitive inhibitor of plasmin. These properties make possible its clinical use as an antifibrinolytic in the treatment of both general and local fibrinolytic hemorrhages.

Tranexamic acid solution for injection is indicated in patients with hemophilia for short-term use (two to eight days) to reduce or prevent hemorrhage and reduce the need for replacement therapy during and following tooth extraction. Other indications may include hereditary angioneurotic edema, hyperfibrinolysis, epistaxis, hyphema, and menorrhagia. Tranexamic acid has also been demonstrated to decrease all-cause mortality and deaths due to hemorrhage in trauma patients. McCluskey et al., Int J Pharm Compounding 2014, 18(5), 432-487.

Tranexamic acid is commercially available in a tablet form and in an injectable intravenous form as CYKLOKAPRON®. Following oral administration, absorption from the human gastrointestinal tract is not complete (40%). CYKLOKAPRON® (Pharmacia and Upjohn Co.) tranexamic acid injection is currently sold in a 100 mg/mL concentration for dilution prior to intravenous administration. Each mL of the sterile solution for intravenous injection contains 100 mg tranexamic acid and 1 mL water for injection (10 wt %). The aqueous solution for injection has a pH of 6.5 to 8.0. For intravenous infusion, CYKLOKAPRON Injection may be mixed with most solutions for infusion such as electrolyte solutions, carbohydrate solutions, amino acid solutions, and Dextran solutions. Immediately before tooth extraction in patients with hemophilia, 10 mg per kg body weight of CYKLOKAPRON is administered intravenously together with replacement therapy. Following tooth extraction, intravenous therapy at a dose of 10 mg per kg body weight three to four times daily, may be used for 2 to 8 days. The label states the diluted mixture should be prepared the same day the solution is to be used. The diluted mixture may be stored for up to 4 hours at room temperature prior to patient administration.

The marketed generic product Tranexamic acid 100 mg/ml solution for injection is provided in ampoules or vials for dilution with, for example, 0.9% sodium chloride solution, 5% glucose solution or Ringer's solution (compound sodium chloride). The required volume of generic concentrated product is added to the chosen infusion solution to achieve final concentrations of 1% or 2% (i.e., 1 gram or of 2 grams in 100 ml). The mixture should be used immediately after preparation, according to label. If storage is necessary, the mixture should be stored at 2° C.-8° C. for a maximum of 24 hours. Mixture not used within 24 hours of preparation should be discarded. Physicochemical stability of the reconstituted solutions of the marketed generic product Tranexamic acid 100 mg/ml in the above diluent's solvents solutions packed in glass and plastic containers has been demonstrated for 24 hours stored at 2° C.-8° C.

The requirement for diluting CYKLOKAPRON® or generic Tranexamic acid 100 mg/ml Solution for Injection before use is associated with a number of disadvantages. One disadvantage is that the diluted solution is only stable for 24 hours at 2° C.-8° C. and only stable for 4 hours at room temperature prior to patient administration. Another disadvantage is that the pH of the diluted formulation varies depending on the choice of diluent. Other disadvantages associated with the dilution step include the potential for contamination, and dosage errors.

Yang et al., CN 106109401 A, provides tranexamic acid injection formulations using water for injection having conductivity of no higher than 0.6 µS/cm at 20° C. and total organic carbon (TOC) of less than 0.4 mg/L or less than 0.35 mg/L. An elaborate water pretreatment method is described.

Stable ready to use injectable tranexamic acid solutions are desirable due to improved convenience and safety compared to tranexamic acid concentrated solutions.

The pharmaceutical compositions and methods described herein overcome these disadvantages. In particular, the ready-to-use, injectable formulations described herein are stable, allow medical personal to use prepared containers containing an injectable formulation off the shelf without additional preparation, avoid potential contamination problems, and eliminate dosage errors.

SUMMARY OF THE INVENTION

Described herein are ready-to-use pharmaceutical compositions of tranexamic acid or pharmaceutically acceptable salts thereof, which are suitable for intravenous administration. By providing ready-to-use pharmaceutical compositions at a specific pH, these pharmaceutical compositions are stable at room temperature for at least one year. When stored at room temperature, the pharmaceutical compositions exhibit between 0% to about 5% loss of drug and between 0% to about 3% (w/w) total impurity formation over an eighteen to twenty four month period.

Additional benefits of the ready-to-use, injectable pharmaceutical compositions include convenience and ease of use as compared to concentrated formulations, improved safety for patients due to elimination of dosage errors and solution contamination, reduction of medical waste, and ease of administration in emergency situations.

Ready-to-use pharmaceutical compositions are provided herein comprising tranexamic acid or pharmaceutically acceptable salts thereof, water, and one or more tonicity agents, and a pH adjuster. In some embodiments, the compositions optionally comprise one or more cosolvents. Tranexamic acid can be present at concentrations between about 0.05 mg/ml to about 15 mg/ml. Typically, the concentration range for tranexamic acid is between about 3 mg/ml to about 12 mg/ml. Optionally, the pharmaceutical compositions can comprise pH adjusters selected from acids and bases.

The pharmaceutical compositions described herein require no dilution prior to administration, and typically have a pH within the range from about 6.0 to about 8.0, and a tonicity between about 270 to about 340 mOsm/kg. The compositions can be administered by parenteral routes, including, subcutaneous, intramuscular, intravenous, intra-atrial, or intra-arterial continuous infusion to a patient. The compositions are suitable for use in patients with hemophilia for short-term use (two to eight days) to reduce or prevent hemorrhage and reduce the need for replacement therapy during and following tooth extraction when oral therapy is not feasible or desirable.

An aqueous pharmaceutical composition is provided for parenteral administration comprising tranexamic acid or a pharmaceutically acceptable salt thereof, and a tonicity agent, wherein the composition requires no dilution before administration and has a pH from 6.0 to 8.0, 7.0 to 8.0, or 7.2 to 7.4. In some embodiments, aqueous pharmaceutical compositions are provided wherein the tranexamic acid is present in a concentration of from 3 to 12 mg per mL. Aqueous pharmaceutical compositions are provided wherein the tranexamic acid is present in a concentration of from 3 to 7 mg per mL, or 4 to 6 mg per mL, or from 8 to 12 mg per mL, or 9 to 11 mg per mL. The aqueous pharmaceutical compositions employ Water for Injection (WFI) having a conductivity at 25° C.≤1.5 µS/cm, or from 0.6 to 1.5 µS/cm, or 0.65 to 1.4 µS/cm by USP <645>. The aqueous pharmaceutical compositions employ WFI having Total Organic Carbon (TOC)<500 ppb, 5-250 ppb, or 10-150 ppb by USP <643>.

The tonicity agent may be selected from the group consisting of sodium chloride, dextrose, sucrose, xylitol, fructose, glycerol, sorbitol, mannitol, potassium chloride, mannose, calcium chloride, and magnesium chloride. In some embodiments, the tonicity agent is in a concentration effective to impart osmolality of from 270 to 340 mOsm/kg. In some embodiments, the tonicity agent is sodium chloride. In some embodiments, the sodium chloride is present in a concentration of from 5-10 mg/mL, or from 6 to 8.5 mg/mL.

The tonicity agent may be mannitol, optionally wherein the mannitol is in a concentration of from 35 to 45 mg per mL.

The tranexamic acid ready to use solutions in aqueous sodium chloride remain stable at a pH selected within the range of from pH 4.0 to pH 11.0 and exhibit greater than 97% of undegraded tranexamic acid compared to initial concentration when stored for at least 6 months at 25° C.±2° C. and 60% RH±5% or 40° C.±2° C. and 75% RH±5%.

The tranexamic acid ready to use solutions in aqueous sodium chloride remain stable at a pH selected within the range of from pH 6.0 to pH 8.0 and exhibit greater than 98% by HPLC of undegraded tranexamic acid compared to initial concentration when stored for at least 6 months at 25° C.±2° C. and 60% RH±5% or 40° C.±2° C. and 75% RH±5%.

The tranexamic acid ready to use compositions are capable of maintaining at least about 90%, 95%, 97%, or 98% of the tranexamic acid in undegraded form after storage for at least 90 days, 120 days, 180 days, 360 days, or 540 days or 730 days at room temperature.

In some embodiments, an a aqueous pharmaceutical composition for parenteral administration comprising: tranexamic acid or a pharmaceutically acceptable salt thereof, water for injection, a tonicity agent, and at least one pH adjuster, optionally selected from the group consisting of hydrochloric acid, sodium hydroxide and a mixture thereof.

In some embodiments, an pharmaceutical composition is provided for intravenous administration comprising a ready-to-use aqueous solution with a pH from about 6.0 to about 8.0 comprising: from about 3 mg/mL to about 12 mg/mL tranexamic acid or a pharmaceutically acceptable salt thereof; a tonicity agent selected from (i) about 35 mg/mL to about 45 mg/mL mannitol or (ii) about 6.8-8.2 mg/mL sodium chloride; and a pH adjuster in an amount to provide initial pH from about 6.0 to about 8.0, 7.0 to 8.0 or 7.3 to 7.5. In some embodiments, the aqueous solution is contained in a pharmaceutically acceptable container. In some embodiments, the aqueous tranexamic acid solution when stored in the container for at least one year at room temperature exhibits (i) less than a 10% decrease in the concentration of tranexamic acid compared to concentration at manufacture, and (ii) a total impurity formation of less than about 3%.

DETAILED DESCRIPTION OF THE INVENTION

Definitions

The singular forms "a", "an" and "the" are intended to include the plural forms as well, unless the context clearly indicates otherwise.

The term "and/or" refers to and encompasses any and all possible combinations of one or more of the associated listed items.

The term "about," as used herein when referring to a measurable value such as an amount of a compound, dose, time, temperature, and the like, is meant to encompass variations within the error of measurement for the specified amount.

Unless otherwise specified, all percentage "%" values are expressed as weight percent compared to total weight of the composition.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs. In the event of conflicting terminology, the present specification is controlling.

The term "therapeutically effective amount" refers to the amount of a compound that, when administered to a subject for treating a disease or condition, is sufficient to effect such treatment to fully or substantially alleviate the symptoms of the disease state or condition. The "therapeutically effective amount" can vary depending on the compound, the disease and its severity, and the condition, age, weight, gender etc. of the subject to be treated. In some embodiments, the effective amount of tranexamic acid is the amount sufficient to prevent or alleviate hemorrhage during and following dental procedures. In some embodiments, the effective amount of tranexamic acid is an amount sufficient to avoid reducing, interrupting or discontinuing anticoagulant, fibrinolytic or thrombolytic therapy in a patient in need thereof during and following dental procedures. In some embodiments, the effective amount of tranexamic acid is an amount sufficient to reduce the need for factor replacement therapy in the patient dining and following dental procedures. In some embodiments, the effective amount of tranexamic acid is an amount sufficient to reduce the need for antifibrinolytic therapy in the patient during and following dental procedures.

The terms "treating" and "treatment" of a disease state or condition include: (i) preventing the disease state or condition, i.e., causing the clinical symptoms of the disease state or condition not to develop in a subject that may be exposed to or predisposed to the disease state or condition, but does not yet experience or display symptoms of the disease state or condition, (ii) inhibiting the disease state or condition, i.e., arresting the development of the disease state or condition or its clinical symptoms, or (iii) relieving the disease state or condition, i.e., causing temporary or permanent regression of the disease state or condition or its clinical symptoms. In some embodiments, the terms "treating" or "treatment" refer to prevention or alleviation of hemorrhage during and following dental procedures.

The terms, "patient", "subject" or "subjects" include but are not limited to humans, the term may also encompass other mammals, or domestic or exotic animals, for example, dogs, cats, ferrets, rabbits, pigs, horses, cattle, birds, or reptiles.

The term "solution" refers to a clear, homogeneous liquid dosage form that contains at least one active pharmaceutical chemical substance dissolved in a solvent or mixture of mutually miscible solvents.

The term "room temperature" refers to controlled room temperature as between 20° C. to 25° C.

Figure 1:
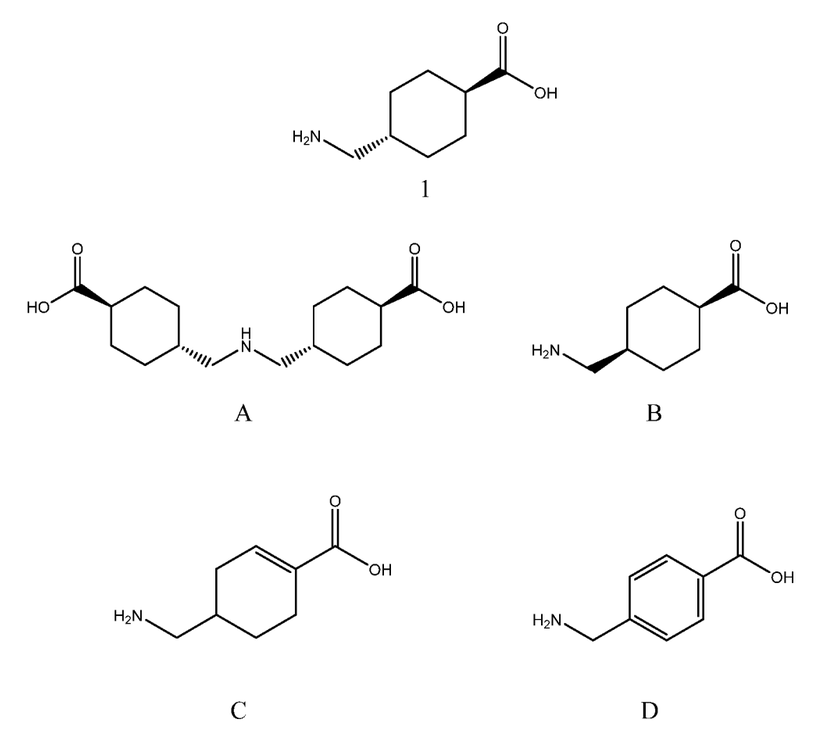
FIG. 1 shows chemical structures of tranexamic acid (1), and tranexamic acid related impurities A, B, C and D.

The term "tranexamic acid related compound A" or "impurity A" refers to trans,trans-4,4'-iminodimethylenedi (cyclohexanecarboxylic acid), also known as tranexamic acid dimer, having CAS RN 93940-19-3. The chemical structure of impurity A is shown in FIG. 1(A).

The term "tranexamic acid related compound B" or "impurity B" refers to cis-4-(aminomethyl)cyclohexanecarboxylic acid, also known as cis-tranexamic acid, having CAS RN: 1197-17-7. The chemical structure of impurity B is shown in FIG. 1(B).

The term "tranexamic acid related compound C" or "impurity C" refers to (RS)-4-(aminomethyl)cyclohex-1-enecarboxylic acid, also known as 1,2-didehydro tranexamic acid, having CAS RN: 330838-52-3. The chemical structure of impurity C is shown in FIG. 1(C).

The term "tranexamic acid related compound D" or "impurity D" refers to 4-(aminomethyl)benzoic acid, also known as benzylamine-4-carboxylic acid, having CAS RN: 56-91-7. The chemical structure of impurity D is shown in FIG. 1(D).

Tranexamic acid, also known as trans-4-(aminomethyl) cyclohexanecarboxylic acid, also referred to as TXA, for example having CAS RN: 1197-18-8, is an antifibrinolytic hemostatic agent used to prevent or treat severe hemorrhage. The chemical structure of tranexamic acid is shown in FIG. 1 (1). Tranexamic acid is useful for local antifibrinolytic therapy for patients with inherited bleeding disorders for dental procedures. When administered 36-48 hours before surgery in four doses of 10-20 mg per kg body weight, an antifibrinolytically active concentration (10 μg/mL) of tranexamic acid remained up to 17 hours in the tissues investigated, and up to 7-8 hours in the serum.

Ready-to-use, stable pharmaceutical compositions comprising tranexamic acid and water for injection are provided herein which are suitable for intravenous administration. The ready-to-use pharmaceutical compositions described herein comprise tranexamic acid or a pharmaceutically acceptable salt thereof as the active ingredient, water, at least one tonicity agent and a pH adjuster.

As used herein, the term "ready-to-use" refers to a premixed pharmaceutical composition that does not require reconstitution or dilution before administration to a patient. In contrast to ampule formulations comprising tranexamic acid that must be diluted prior to use in a diluent and container selected by hospital personnel, the ready-to-use pharmaceutical compositions provided herein are stable at room temperature for 6 months or longer. In some embodiments, suitable buffers and/or co-solvents may be added to the pharmaceutical compositions. In some embodiments, no buffer and/or no co-solvent is employed.

All patents, patent applications and publications referred to herein are incorporated by reference in their entirety.

Compositions

Pharmaceutical compositions in the form of ready-to-use intravenous solutions comprising tranexamic acid are described herein.

In some embodiments, the ready-to-use pharmaceutical compositions comprise one or more tonicity agents. Typically, tonicity agents are used to adjust the osmolality of the ready-to-use pharmaceutical compositions to bring it closer to the osmotic pressure of body fluids, such as blood or plasma. In some embodiments, the tonicity of the ready-to-use formulation can be modified by adjusting the concentration of other components present in the ready-to-use formulation. Provided that the compositions are physiologically compatible, the compositions do not require any particular osmolality. Thus, the compositions can be hypotonic, isotonic or hypertonic. In some preferred embodiments, the compositions are isotonic with blood with range of 270-340 mOsmol/Kg. Typically the ready-to-use pharmaceutical compositions have a tonicity between about 270 to about 340 mOsm/Kg, about 280 to about 330 mOsm/Kg, or about 290 to about 310 mOsm/Kg.

Suitable tonicity agents for use in the ready-to-use pharmaceutical compositions include, but are not limited to, anhydrous or hydrous forms of sodium chloride, dextrose, sucrose, xylitol, fructose, glycerol, sorbitol, mannitol, potassium chloride, mannose, calcium chloride, magnesium chloride and other inorganic salts. The quantity of the tonicity agent in the formulation can be expressed in mg/ml or in g/L. In typical embodiments, the tonicity agent(s) is present from about 1 mg/ml to about 90 mg/ml. Thus, the ready-to-use pharmaceutical compositions can comprise one or more tonicity agents at about 1-5 mg/ml, at about 5-10 mg/ml, at about 10-15 mg/ml, at about 15-25 mg/ml, at about 25-50 mg/ml, at about 50-60 mg/ml, at about 60-70 mg/ml, at about 70-80 mg/ml, and at about 80 to 90 mg/ml, as well as combinations of the above ranges.

In some embodiments, the tonicity agent is sodium chloride. The ready-to-use pharmaceutical composition may comprise sodium chloride in a concentration of from about 0.68 to about 0.82% wt/vol, from about 0.79 to about 0.82%, or from about 0.68 to about 0.74% wt/vol. The ready-to-use pharmaceutical composition may comprise sodium chloride in a concentration of from about 5 mg/mL to about 9 mg/mL, or from about 6 to about 8.5 mg/mL. In some embodiments, the amount of sodium chloride in the formulations is determined based on experimentally established osmolality of 32 mOsm/kg and 64 mOsm/kg of tranexamic acid in water for injection at 5 mg/ml and 10 mg/ml, respectively. In some embodiments, the amount of sodium chloride in aqueous tranexamic acid 5 mg/mL is 7.8 to 8.4 mg/mL NaCl, or 8.0 to 8.2 mg/ml NaCl. In some embodiments, the amount of sodium chloride in aqueous tranexamic acid 10 mg/mL is 6.8 to 7.5 mg/ml NaCl, or 7.0 to 7.3 mg/mL NaCl.

In some embodiments, the tonicity agent is mannitol. The ready-to-use pharmaceutical composition may comprise mannitol is in a concentration of from about 30 to about 50 mg/mL, about 35 to about 45 mg per mL, or about 38 to about 43 mg/mL.

In some embodiments, the ready-to-use pharmaceutical compositions further comprise a pH adjuster. Suitable pH adjusters typically include at least an acid or a salt thereof, and/or a base or a salt thereof. Acids and bases are added on an as needed basis in order to achieve a desired pH. For example, if the pH is greater than the desired pH, an acid is used to lower the pH to the desired pH. Acids suitable for use in ready-to-use pharmaceutical compositions include, but are not limited to, hydrochloric acid, phosphoric acid, citric acid, ascorbic acid, acetic acid, sulphuric acid, carbonic acid and nitric acid. In some embodiments, hydrochloric acid is used to adjust the pH. By way of another example, if the pH is less than the desired pH, a base is used to adjust the pH to the desired pH. Bases suitable for use in ready-to-use pharmaceutical compositions include, but are not limited to, sodium hydroxide, potassium hydroxide, calcium hydroxide, sodium carbonate, sodium citrate, sodium acetate, and magnesium hydroxide. In some embodiments, sodium hydroxide is used to adjust the pH.

In some embodiments, the pH adjuster is any pharmaceutically acceptable pH adjuster known in the art. In some embodiments, the pH adjuster is selected from phosphoric acid, hydrochloric acid, nitric acid, sulfuric acid, hydrobromic acid, citric acid, malic acid, adipic acid, ascorbic acid, tartaric acid, lactic acid, phosphoric acid and combinations thereof. In some embodiments, the pH adjuster is hydrochloric acid. The pH adjuster may be employed in the composition in an amount in the range of about 0.1 wt % to 1 wt %, or about 0.2 to 0.5 wt %, or about 0.3 to 0.4 wt % to adjust the pH range as specified.

Tranexamic acid in a ready-to-use intravenous solution may be provided with or without a pH adjuster in a range from pH 4.0 to 11.0, pH 4.5 to 10.0, pH 5.0 to 9.0, pH 5.5 to 8.5, pH 6.0 to 8.0, pH 7.0 to 8.0, or pH 7.3 to 7.5, or about pH 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0, or any pH value in between. In one specific embodiment, the pH is about 7.3. In another specific embodiment, the pH is about 7.4. In some embodiments, a pH adjuster is employed in the tranexamic aqueous formulations to adjust the pH.

In some embodiments, the ready-to-use pharmaceutical compositions further comprises a buffer. In some embodiments, no buffer is employed.

Buffers suitable for use in the pharmaceutical compositions described herein include, but are not limited to, pharmaceutically acceptable salts and acids of acetate, glutamate, citrate, tartrate, benzoate, lactate, histidine or other amino acids, gluconate, phosphate, malate, succinate, formate, propionate, and carbonate. "Pharmaceutically acceptable" is used herein in the sense of being compatible with the other ingredients of the formulation and not deleterious to the recipient thereof. Accordingly, the term "pharmaceutically acceptable salt" references salt forms of the active compounds which are prepared with counter ions which are non-toxic under the conditions of use and are compatible with a stable formulation. The concentration of the buffer in the formulation can be expressed in mg/ml, g/L or as a molar concentration. Optionally, the composition may comprise from about 0.0001 mg/ml to about 100 mg/ml of a suitable buffer is present in the pharmaceutical compositions. Thus, the ready-to-use pharmaceutical compositions can comprise from about 0.0001 to about 0.001 mg/ml of a suitable buffer, from about 0.001 to about 0.01 mg/ml of a suitable buffer, from about 0.01 to about 0.1 mg/ml of a suitable buffer, from about 0.1 to 1 mg/ml of a suitable buffer, from about 1 to about 5 mg/ml of a suitable buffer, from about 5 to about 10 mg/ml of a suitable buffer, from about 10 to about 15 mg/ml of a suitable buffer, from about 15 to about 20 mg/ml of a suitable buffer, from about 20 to about 25 mg/ml of a suitable buffer, from about 25 to about 50 mg/ml of a suitable buffer, from about 50 to about 75 mg/ml of a suitable buffer, and from about 75 to about 100 mg/ml of a suitable buffer.

Alternatively, the buffer concentration can be expressed as molar concentrations. In typical embodiments, from about 0.1 to 100 mM of a suitable buffer is present in the pharmaceutical compositions. Thus, the ready-to-use pharmaceutical compositions can comprise a suitable buffer having a concentration from about 0.1 to about 100 mM, from about 0.1 to about 0.5 mM, from about 0.5 to about 1.0 mM, from about 1.0 to about 5 mM, from about 5 to about 10 mM, from about 10 to about 15 mM, from about 15 to about 25 mM, from about 25 to about 50 mM, from about 50 to about 75 mM, and from about 75 to about 100 mM.

The ready-to-use Tranexamic acid 5 mg/ml or 10 mg/ml compositions may be autoclaved in its final container.

In some embodiments, the compositions provided herein capable of maintaining at least about 90%, 95%, 97.5%, 98%, 99%, 99.5%, or 99.7% of the release, or "as manufactured," amount of tranexamic acid in undegraded form after storage for at least 6 months at 25° C. at 40% relative humidity when measured by liquid chromatography, e.g., HPLC by USP <621>. In some embodiments, the compositions provided herein capable of maintaining at least about 90%, 95%, 97.5%, 98%, 99%, or 99.5% of the release, or "as manufactured," amount of tranexamic acid in undegraded form after storage for at least 12 months at 25° C. at 40% relative humidity when measured by liquid chromatography. In some embodiments, the compositions provided herein capable of maintaining at least about 90%, 95%, 97.5%, 98%, 99%, 99.5% of the release, or "as manufactured," amount of tranexamic acid in undegraded form after storage for at least 18 months at 25° C. at 40% relative humidity when measured by liquid chromatography. In some embodiments, the compositions provided herein capable of maintaining at least about 90%, 95%, 97.5%, 98%, 99% of the release, or "as manufactured," amount of tranexamic acid in undegraded form after storage for at least 24 months at 25° C. at 40% relative humidity when measured by liquid chromatography. In some embodiments, the compositions provided herein capable of maintaining at least about 90%, 95%, 97.5%, 98%, 99% of the release, or "as manufactured," amount of tranexamic acid in undegraded form after storage for at least 36 months at 25° C. at 40% relative humidity when measured by liquid chromatography. In some embodiments, the compositions provided herein capable of maintaining at least about 90%, 95%, 97.5%, 98% of the release, or "as manufactured," amount of tranexamic acid in undegraded form after storage for at least 48 months at 25° C. at 40% relative humidity when measured by liquid chromatography.

In some embodiments, the compositions provided herein capable of maintaining at least about 90%, 95%, 97.5%, 98%, 99%, 99.5%, or 99.7% of the release, or "as manufactured," amount of tranexamic acid in undegraded form after storage for at least 6 months at 40° C. at 25% relative humidity when measured by liquid chromatography. In some embodiments, the compositions provided herein capable of maintaining at least about 90%, 95%, 97.5%, 98%, 99%, 99.5%, 99.7%, or 99.8% of the release, or "as manufactured," amount of tranexamic acid in undegraded form after storage for at least 12 months at 40° C. at 25% relative humidity when measured by liquid chromatography. In some embodiments, the compositions provided herein capable of maintaining at least about 90%, 95%, 97%, 97.5%, 98%, 99%, 99.5%, 99.7%, or 99.8% of the release, or "as manufactured," amount of tranexamic acid in undegraded form after storage for at least 18 months at 40° C. at 25% relative humidity when measured by liquid chromatography.

The ready-to-use compositions can be packaged for use in a variety of pharmaceutically acceptable containers. The compositions are preferably packaged in a pharmaceutically acceptable container selected from vial, intravenous bag or bottle. In some embodiments, packages can be used that reduce the amount of light which can reach the composition. For example, in some embodiments, the container may, optionally, further comprise a light barrier, such as an aluminum overpouch or a carton.

In some embodiments, the ready-to-use pharmaceutical compositions are dispensed in a pharmaceutically acceptable container such as plastic intravenous bags, including pre-mix bags and admix bags or bottles. Intravenous bags are well known in the art and commercially available. Examples of commercially available intravenous bags include, but are not limited to: ADDEASE®, ADD-VANTAGE®, BFS™, DUPLEX™, EXCEL®, FIRST CHOICE™ GALAXY®, INTRAVIA®, PROPYFLEX™, SOLOMIX®, STEDIM® 71, STEDIM®100, VIAFLEX®, VIAFLO™, and VISIV®. In some embodiments, the pharmaceutical compositions are provided in intravenous containers comprising a polymeric contact surface comprising ethylene-propylene copolymer (e.g., EXCEL), polyethylene (e.g., GALAXY), polyolefin blend (e.g. VISIV and VIAFLO), PVC (VIAFLEX and INTRAVIA), or ethylene-vinylacetate (EVA) (e.g., STEDIM®71).

In another embodiment, the pharmaceutical compositions are packaged in ethylene/propylene copolymer (EXCEL®) plastic containers.

In some embodiments, the components of the bag that come into contact with the pharmaceutical compositions should not contain polar polymers, such as polyvinyl chloride (PVC) and ethylene vinyl acetate (EVA). Examples of bags that do not contain polar polymers and thus, are suitable for use in these embodiments, include, but are not limited to, GALAXY®, EXCEL®, VISIV®, and VIAFLO™.

In some embodiments, the pharmaceutical compositions are packaged in a glass container. In some embodiments, the pharmaceutical compositions are packaged in USP Type I borosilicate glass vials or USP Type II soda lime silica glass vials. The glass vials may be clear or amber glass vials. The glass vials may be size 50 mL, 100 mL, or 200 mL vials.

The glass vials may have a USP Elastomer Closure for Injections under <381> elastomeric stopper. The stopper may be selected from a butyl, EPDM, natural rubber, nitrile or silicone material. The butyl stopper may be selected from a chlorobutyl or bromobutyl stopper. The stopper or cap may be coated with a silicone, B2 crosslinked coating, Flurotec coating, Teflon coating, Westar RS treatment, RTS treatment, or thermoplastic elastomer (TPE) product. In some embodiments, the glass vial is closed with a bromobutyl stopper and sealed with aluminum caps.

Procedures for filling pharmaceutical compositions in pharmaceutically acceptable containers, and their subsequent processing are known in the art. These procedures can be used to produce sterile pharmaceutical drug products often required for health care. See, e.g., Center for Drug Evaluation and Research (CDER) and Center for Veterinary Medicine (CVM), "Guidance for Industry for the Submission Documentation for Sterilization Process Validation in Applications for Human and Veterinary Drug Products", (November 1994). Examples of suitable procedures for producing sterile pharmaceutical drug products include, but are not limited to, terminal moist heat sterilization, ethylene oxide, radiation (i.e., gamma and electron beam), and aseptic processing techniques. Any one of these sterilization procedures can be used to produce the sterile pharmaceutical compositions described herein.

In some embodiments, sterile pharmaceutical compositions can be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the compositions can be sterile filled into a container to avoid the heat stress of terminal sterilization.

In some embodiments, the compositions are terminally sterilized using moist heat. Terminal sterilization can be used to destroy all viable microorganisms within the final, sealed container containing the pharmaceutical composition. An autoclave is typically used to accomplish terminal heat-sterilization of drug products in their final packaging. Typical autoclave cycles in the pharmaceutical industry to achieve terminal sterilization of the final product are 121° C. for at least 10 minutes.

The ready-to-use, isotonic composition comprising tranexamic acid may be provided in a 5 mg/ml concentration in water for injection comprising a tonicity agent and a pH adjuster in a 100 ml volume. This will provide a 500 mg dose of tranexamic acid.

The ready-to-use, isotonic composition comprising tranexamic acid may be provided in a 5 mg/ml concentration in water for injection comprising a tonicity agent and a pH adjuster in a 200 ml volume. This will provide a 1,000 mg dose of tranexamic acid.

The ready-to-use, isotonic composition comprising tranexamic acid may be provided in a 10 mg/ml concentration in water for injection comprising a tonicity agent and a pH adjuster in a 50 ml volume. This will provide a 500 g dose of tranexamic acid.

The ready-to-use, isotonic composition comprising tranexamic acid may be provided in a 10 mg/ml concentration in water for injection comprising a tonicity agent and a pH adjuster in a 100 ml volume. This will provide a 1,000 g dose of tranexamic acid.

The ready-to-use, isotonic composition comprising tranexamic acid may be provided in a 10 mg/ml concentration in water for injection comprising a tonicity agent and a pH adjuster in a 200 ml volume. This will provide a 2,000 mg dose of tranexamic acid.

Analytical Procedures

In some embodiments, ready-to-use tranexamic compositions are provided that pass the Particulate matter test under USP<788> when stored at room temperature for at least 3 months, 6 months, 12 months, 18 months or more.

In some embodiments, ready-to-use tranexamic compositions are provided that pass the pH test under USP<791> with variation±0.5 pH unit compared to original pH when stored at room temperature for at least 3 months, 6 months, 12 months, 18 months or more.

In some embodiments, ready-to-use tranexamic compositions are provided that pass the Completeness of Solution Test under USP<641>, exhibiting a clear solution when stored at room temperature for at least 3 months, 6 months, 12 months, 18 months or more.

In some embodiments, ready-to-use tranexamic compositions are provided that pass the Visible Particles test under USP<790>, exhibiting absence of visible particles when stored at room temperature for at least 3 months, 6 months, 12 months, 18 months or more.

In some embodiments, ready-to-use tranexamic compositions are provided that pass the Color of Solution or Degree of Coloration test under Ph Eur 2.2.2, exhibiting colorless solution when stored at room temperature for at least 3 months, 6 months, 12 months, 18 months or more.

In some embodiments, ready-to-use tranexamic compositions are provided that exhibit tranexamic acid by HPLC of 95.0-105.0% of initial value under USP<621> when stored at room temperature for at least 3 months, 6 months, 12 months, 18 months or more.

In some embodiments, ready-to-use tranexamic compositions are provided that exhibit not more than 0.1% tranexamic acid related impurity A by HPLC under USP<621> when stored at room temperature for at least 3 months, 6 months, 12 months, 18 months or more.

In some embodiments, ready-to-use tranexamic compositions are provided that exhibit not more than 0.2% tranexamic acid related impurity B by HPLC under USP<621> when stored at room temperature for at least 3 months, 6 months, 12 months, 18 months or more.

In some embodiments, ready-to-use tranexamic compositions are provided that exhibit not more than 0.1% tranexamic acid related impurity C by HPLC under USP<621> when stored at room temperature for at least 3 months, 6 months, 12 months, 18 months or more.

In some embodiments, ready-to-use tranexamic compositions are provided that exhibit not more than 0.1% tranexamic acid related impurity D by HPLC under USP<621> when stored at room temperature for at least 3 months, 6 months, 12 months, 18 months or more.

In some embodiments, ready-to-use tranexamic compositions are provided that exhibit not more than 0.1% of any single unidentified impurity by HPLC under USP<621> when stored at room temperature for at least 3 months, 6 months, 12 months, 18 months or more.

In some embodiments, ready-to-use tranexamic compositions are provided that exhibit not more than 0.4% total impurities by HPLC under USP<621> when stored at room temperature for at least 3 months, 6 months, 12 months, 18 months or more.

In some embodiments, ready-to-use tranexamic compositions are provided that exhibit not more than Total Aerobic Microbial Count (TAMC) of ≤10 cfu/100 ml by USP <61> when stored at room temperature for at least 3 months, 6 months, 12 months, 18 months or more.

In some embodiments, ready-to-use tranexamic compositions are provided that exhibit not more than Total Yeast and Molds Count (TYMC) of ≤10 cfu/100 ml by USP <61> when stored at room temperature for at least 3 months, 6 months, 12 months, 18 months or more.

In some embodiments, ready to use tranexamic compositions are provided that exhibit ≤35 IU/ml Endotoxins by USP<85>, at manufacture and when stored at room temperature for at least 3 months, 6 months, 12 months, 18 months or more.

In some embodiments, ready to use tranexamic compositions are provided that are sterile by USP <71>, at manufacture and when stored at room temperature for at least 3 months, 6 months, 12 months, 18 months or more.

In some embodiments, ready to use tranexamic compositions are provided that are pH 6.0-8.0 by USP <791>, at manufacture and when stored at room temperature for at least 3 months, 6 months, 12 months, 18 months or more.

Manufacturing

In some embodiments, the manufacturing process for ready-to-use compositions is a non-aseptic process with terminal sterilisation. Facilities, equipment, procedures and personnel for processing are according to the European and GMP rules for non-aseptic process. The filter of the solution may be 0.22 μm hydrophilic filter for example, as suitable for substances that are easily soluble in water. Tranexamic acid is sensitive to oxidation and to light. Therefore, in some embodiments, the API, the bulk solution and the filled vials are protected as much as possible from light. The amount of Tranexamic acid in batch formula is adjusted according to the desired final concentration.

For compounding of the ready-to-use solution, the process comprises introducing about 90% of water for injection of the batch formula into the compounding vessel; bubbling 0.22 μm filtered nitrogen into the water for injection until dissolved oxygen level is ≤0.5 ppm; adding tranexamic acid in divided portions until complete dissolution; adding sodium chloride and stirring under $N_2$ until dissolution complete; adjusting pH by adding a pH adjuster; and stirring under nitrogen bubbling until dissolved oxygen is ≤0.5 ppm. In some embodiments, the pH is adjusted with 0.1-1M sodium hydroxide or 0.1-1M hydrochloric acid 1M to 7.4. (limit: 7.3-7.5). The oxygen level: ≤0.5 ppm. Appearance of the solution by visual inspection: clear and particle free. pH: 7.3-7.5. Content in Tranexamic acid: 97-103 mg/ml (97-103%). Bioburden of bulk solution: bacteria: 10 cfu/100 ml. Fungi: 10 cfu/100 ml. The solution is filtered through 0.22 μm filter by 0.22 μm filtered nitrogen pressure in the compounding vessel.

Vials are washed, rinsed, sterilized and endotoxins are inactivated. Stoppers are acquired ready to use from the supplier. The solution is filled into the vials that are closed by the stopper and are sealed by aluminum caps. Vials are sterilised at 121° C. during 20 minutes.

In-process controls include pre-sterilisation bioburden of the solution into the vials. Bacteria: 10 cfu/100 ml. Fungi: 10 cfu/100 ml, verification of conformity of the sterilization cycle, and control of closure integrity. The product is analysed according to the analytical procedures in Table 1A.

TABLE 1A

Analytical procedures for the tests:

Appearance (Visual inspection)
Appearance of the solution (USP <641>)
Appearance of the solution (USP <790>)
Identification of Tranexamic acid by HPLC (USP <621>)
pH (USP <791>)
Deliverable volume (USP <697>)
Particulate matter (USP <788>)
Bacterial endotoxins (USP <85>)
Sterility (USP <71>)

Specifications of the finished product are shown in Table 1B.

TABLE 1B

Specifications for Ready-to-Use Tranexamic Acid Intravenous

| TEST | SPECIFICATION AT RELEASE AND AT SHELF LIFE in compliance with USP <1> |
|---|---|
| Appearance (Visual inspection) | Colourless liquid filled into colourless glass vial |
| Appearance of the solution (USP <641>) | Clear liquid |
| Appearance of the solution (USP <790>) | Free from visible particulate matter |

TABLE 1B-continued

Specifications for Ready-to-Use Tranexamic Acid Intravenous

| TEST | SPECIFICATION AT RELEASE AND AT SHELF LIFE in compliance with USP <1> | | | |
|---|---|---|---|---|
| Identification: | | | | |
| Tranexamic acid by HPEC (USP <621>) | Same retention time as standard | | | |
| Tranexamic acid by UV (USP <857>) | Same spectra of standard | | | |
| pH (USP <791>) | 6.0-8.0 | | | |
| Deliverable volume (USP <697>) | 50 ml: 100 ml: 200 ml: | | | |
| Particulate matter (USP <788>) | Per container ≥10 μm: ≥25 μm: | 50 ml 3000 300 | 100 ml 3000 300 | 200 ml 2400 400 |
| Impurities by HPEC (USP <621>) | | | | |
| Impurity A | ≤0.1% | | | |
| Impurity B | ≤0.2% | | | |
| Impurity C | ≤0.1% | | | |
| Impurity D | ≤0.1% | | | |
| Any other impurity | ≤0.1% | | | |
| Total impurities | ≤0.4% | | | |
| Assay Tranexamic acid by HPLC (USP <621>) | 95.0%-105.5% | | | |
| Bacterial endotoxins (USP <85>) | ≤35 IU/ml | | | |
| Sterility (USP <71>) | Sterile | | | |

Additionally, identification of Tranexamic acid by UV may be performed according to USP <857>. Prepare test and standard solutions at 0.05 mg/ml of Tranexamic acid. Make zero with WFI. Perform UV spectra from 200 to 400 nm. Both spectra should be similar.

Administration

The ready to use tranexamic compositions are intended for intravenous administration The intravenous administration may be selected from one or more of intravenous injection and infusion. The intravenous injection may be selected from one, two, three, four or more times per day. The ready to use compositions may be administered without dilution at 2.5 to 5 mL/min at 10 mg/mL may be administered at about 5 mL/min.

In some embodiments, the composition is administered intravenously at about 2 mg/kg to about 30 mg/kg, or about 10 mg/kg to about 15 mg/kg body weight. In some embodiments, the dose is from about 200 mg to about 2,000 mg, or about 500 mg to about 1,000 mg tranexamic acid.

The ready to use tranexamic compositions may be used in patients with a coagulopathy, such as hemophilia, for short-term use (two to eight days) to reduce or prevent hemorrhage and reduce the need for replacement therapy during and following tooth extraction. Specifically, immediately before tooth extraction in patients with coagulopathy, the composition may be administered at about 10 mg/kg body weight intravenously, for example together with replacement therapy. Following tooth extraction, intravenous therapy at a dose of 10 mg/kg body weight three to four times daily may be used for 2 to 8 days.

Other indications may include adult cardiac surgery, adult total knee arthroplasty, adult total hip arthroplasty, hereditary angioneurotic edema, hyperfibrinolysis, epistaxis, hyphema, and menorrhagia. The ready to use tranexamic compositions may be used in trauma patients with significant hemorrhage.

EXAMPLES

Example 1. Study of Osmolality of Solutions of Tranexamic Acid 5 mg/ml and 10 mg/ml The osmolality of solutions of Tranexamic acid 5 mg/ml and 10 mg/ml was measured in order to verify if the formulations can only be by dissolution of Tranexamic acid in the solvent water for injection. The objective was to prepare ready to use isotonic compositions comprising tranexamic acid with osmolality in range of 270-340 mOsmol/Kg. Three solutions of 100 ml of each of Tranexamic acid 5 mg/ml and other three of 10 mg/ml were prepared by dissolution of Tranexamic acid in water for injection. The prepared solutions were filled into 100 ml glass vials and are autoclaved at 121° C. during 20 minutes. The Osmolality of the solutions was measured. Results are shown in Table 1C.

TABLE 1C

Osmolality of Tranexamic acid in Water for Injection

| Solutions | 5 mg/mL | 10 mg/mL |
|---|---|---|
| 1 | 32 mOsmol/Kg | 65 mOsmol/Kg |
| 2 | 31 mOsmol/Kg | 64 mOsmol/Kg |
| 3 | 33 mOsmol/Kg | 63 mOsmol/Kg |
| Average | 32 mOsmol/Kg | 64 mOsmol/Kg |

Conclusion:

The objective is a Tranexamic injection that is isotonic with blood with range of 270-340 mOsmol/Kg. Therefore, formulations cannot be achieved by dissolution of Tranexamic acid in the solvent water for injection alone in view of strongly hypotonic results. Therefore, isotonic agent was required in the formulation.

Example 2. Formulation Development

First, calculations were made of the amounts of sodium chloride and mannitol needed for isotonic preparation in the presence of tranexamic acid. An isotonic preparation range is 270-340 mOsmol/Kg in water for injection (WFI).

To calculate the amount of sodium chloride needed for preparing an isotonic solution of Tranexamic acid 5 mg/ml, a calculation was made on basis of osmolality of 32 mOsmol/Kg of Tranexamic acid 5 mg/ml. For a 900 mg/100 ml of sodium chloride (0.9%), the osmolality is 308 mOsmol/Kg. 900/308×(308−32)=806.49. Therefore 806 mg of sodium chloride was used for preparing 100 ml of a solution of 5 mg/ml Tranexamic acid.

To calculate the amount of sodium chloride needed for preparing an isotonic solution of Tranexamic acid 10 mg/ml, a calculation was made on basis of osmolality of 64 mOsmol/Kg of Tranexamic acid 10 mg/ml. For a 900 mg/100 ml of sodium chloride (0.9%), the osmolality is 308 mOsmol/Kg. 900/308×(308−64)=714.98. Therefore 715 mg of sodium chloride was used for preparing 100 ml of a solution of 10 mg/ml Tranexamic acid.

To calculate the amount of mannitol needed for preparing an isotonic solution of Tranexamic acid 5 mg/ml, a calculation was made on basis of osmolality of 32 mOsmol/Kg of Tranexamic acid 5 mg/ml. For a 5000 mg/100 ml of mannitol (5%), the osmolality is 296 mOsmol/Kg. 5000/296×(296−32)=4459.46. Therefore 4460 mg of mannitol was used for preparing 100 ml of a solution of 5 mg/ml tranexamic acid.

To calculate the amount of sodium chloride needed for preparing an isotonic solution of Tranexamic acid 10 mg/ml, a calculation was made on basis of osmolality of 64 mOsmol/Kg of Tranexamic acid 10 mg/ml. 5000 mg/100 ml of mannitol (5%): osmolality is 296 mOsmol/Kg. 5000/296×(296−64)=3918.92. Therefore 3919 mg of mannitol was used for preparing 100 ml of a solution of 10 mg/ml tranexamic acid.

The osmolality of the formulations of Tranexamic acid 5 mg/ml and 10 mg/ml with the calculated amount of isotonic agent sodium chloride and mannitol was experimentally measured and verified in next step of formulation development studies. Adjustment was performed as needed to obtain target osmolality.

1. A solution of 100 ml of Tranexamic acid 5 mg/ml was prepared as follows.

Dissolution of Tranexamic acid did not occur immediately at addition into WFI but required some time. Even when it appeared that dissolution was achieved, detailed visual observation shows that some grains of the powder were still not quite solubilized. Therefore, dissolution of Tranexamic acid in water was performed by adding tranexamic acid into WFI by portions with addition of one portion after dissolution of the previous. At the end of tranexamic acid addition, stirring was maintained during 15 minutes to ensure complete dissolution. Tranexamic acid was added first followed by other ingredient(s) of the formulation. The pH at the end of dissolution of the 5 mg/ml tranexamic acid solution required about 10 minutes for pH stabilization at pH 5.6.

2. A solution of 100 ml of Tranexamic acid 10 mg/ml was prepared as follows.

1000 mg of Tranexamic acid was added under stirring to 100 ml of water for injection (WFI) until complete dissolution was achieved. A dissolution profile in WFI had same observation as above for the 5 mg/ml, except the pH stabilization is faster than for 5 mg/ml and required about 2-3 minutes. The 10 mg/ml tranexamic acid solution was pH 5.6.

Formulations of tranexamic acid at 5 mg/mL and 10 mg/mL in isotonic sodium chloride and mannitol were prepared as follows.

3. A formulation of Tranexamic acid 5 mg/ml with isotonic agent sodium chloride was prepared according to Table 2.

TABLE 2

Tranexamic acid 5 mg/ml with isotonic agent sodium chloride

| Ingredient | Formulation per 1 ml | Formulation per 100 ml |
|---|---|---|
| Tranexamic acid | 5 mg | 500 mg |
| Sodium chloride | 8.06 mg | 806 mg |
| Water for injection | ad 1 mL | ad 100 mL |

100 ml of a tranexamic acid 5 mg/ml solution was prepared by dissolution first of Tranexamic acid and then sodium chloride according to the above techniques. The pH of the preparation quickly stabilized to 7.2.

4. A formulation of Tranexamic acid 10 mg/ml with isotonic agent sodium chloride was prepared according to Table 3.

TABLE 3

Tranexamic acid 10 mg/ml with isotonic agent sodium chloride

| Ingredient | Formulation per 1 ml | Formulation per 100 ml |
|---|---|---|
| Tranexamic acid | 10 mg | 1000 mg |
| Sodium chloride | 7.15 mg | 715 mg |
| Water for injection | ad 1 mL | ad 100 mL |

100 ml of a tranexamic acid 10 mg/ml solution was prepared by dissolution first of Tranexamic acid and then sodium chloride according to the techniques above. The pH of the preparation quickly stabilized to 7.3.

5. A formulation of Tranexamic acid 5 mg/ml with isotonic agent mannitol was prepared according to Table 4.

TABLE 4

Tranexamic acid 5 mg/ml with isotonic agent mannitol

| Ingredient | Formulation per 1 ml | Formulation per 100 ml |
|---|---|---|
| Tranexamic acid | 5 mg | 500 mg |
| Mannitol | 44.60 mg | 4460 mg |
| Water for injection | ad 1 mL | ad 100 mL |

100 ml of a tranexamic acid 5 mg/ml solution was prepared by dissolution first of Tranexamic acid and then mannitol according to the techniques above. The pH of the preparation relatively quickly stabilized to 5.8.

6. A formulation of Tranexamic acid 10 mg/ml with isotonic agent mannitol was prepared according to Table 5.

TABLE 5

Tranexamic acid 10 mg/ml with isotonic agent mannitol

| Ingredient | Formulation per 1 ml | Formulation per 100 ml |
|---|---|---|
| Tranexamic acid | 10 mg | 1000 mg |
| Mannitol | 39.19 mg | 3919 mg |
| Water for injection | ad 1 mL | ad 100 mL |

100 ml of a tranexamic acid 10 mg/ml solution was prepared by dissolution first of Tranexamic acid and then mannitol after according to the techniques above. The pH of the preparation relatively quickly stabilized to 5.8.

Each of the above preparations was filled into vials of 25 ml and autoclaved at 121° C. during 20 minutes. Used vials of multiple use that had been washed and sterilized several times were employed to ensure that no significant release from the glass vial would go into the preparation. Stability of the preparation was followed up until 5 weeks for the aspect, particles by visual inspection and pH. Results: Aspect and particles by visual inspection: conform. No change is observed. pH stability up to 5 weeks is shown in Table 6.

TABLE 6

Preliminary pH Stability Test

| Tranexamic acid Solution | Initial | After sterilization | 1 weeks | 3 weeks | 4 weeks | 5 weeks |
|---|---|---|---|---|---|---|
| 5 mg/mL | 5.6 | 5.9 | 6.1 | 5.7 | 5.8 | 5.9 |
| 10 mg/mL | 5.6 | 6.0 | 6.4 | 6.1 | 6.1 | 6.0 |
| 5 mg/mL, NaCl | 7.2 | 7.1 | 7.0 | 6.9 | 7.0 | 6.8 |
| 10 mg/mL, NaCl | 7.3 | 7.5 | 7.6 | 7.2 | 7.3 | 7.1 |
| 5 mg/mL, Mannitol | 5.8 | 7.8 | 7.8 | 6.8 | 7.1 | 6.8 |
| 10 mg/mL, Mannitol | 5.8 | 6.9 | 7.0 | 6.8 | 7.1 | 6.8 |

In the preliminary pH stability test, minor pH variations were observed in general, which is likely due to the fact that Tranexamic acid is an amino acid with acid and base functions. However, formulations with sodium chloride exhibited significantly less pH variability than formulations with mannitol, mainly after sterilization, but also over time. The initial pH of formulations with sodium chloride was about pH 7 without pH adjustment, which is close to blood pH 7.4. Sodium chloride was selected as tonicity agent for further formulation development.

Example 3. Formulations-Preliminary 3 Month Stability Data of Finished Formulations After development of formulations of Tranexamic acid 5 mg/ml and 10 mg/ml, a stability study of 3 months' time at laboratory level was performed as preliminary study to check the suitability of developed formulations.

Preparation of the Solutions 500 ml of each formulation of Tables 7 and 8 were prepared as described above, and pH adjusters 1M Sodium hydroxide solution and 1M hydrochloric solution were employed to adjust to pH 7.4, as shown in Table 7 and Table 8.

TABLE 7

Tranexamic acid 5 mg/ml with isotonic agent sodium chloride pH 7.4
Tranexamic acid RTU 5 mg/mL

| Ingredient | Formulation per 1 ml |
|---|---|
| Tranexamic acid | 5 mg |
| Sodium chloride | 8.1 mg |
| NaOH 0.1M | q.s. pH = 7.4 |
| HCl 0.1M | q.s. pH = 7.4 |
| Water for injection | Ad 1.0 ml |

TABLE 8

Tranexamic acid 10 mg/ml with isotonic agent sodium chloride pH 7.4
Tranexamic acid RTU 10 mg/mL

| Ingredient | Formulation per 1 ml |
|---|---|
| Tranexamic acid | 10 mg |
| Sodium chloride | 7.2 mg |
| NaOH 0.1M | q.s. pH = 7.4 |
| HCl 0.1M | q.s. pH = 7.4 |
| Water for injection | Ad 1.0 ml |

Each formulation was filled in 50 ml type I glass vial, closed by bromobutyl stopper and sealed with aluminum caps. Tranexamic acid RTU 5 mg/ml: 10 vials. Tranexamic acid RTU 10 mg/ml: 10 vials. All vials were sterilized in steam autoclave at 121° C. during 20 minutes. The Vials were stored at 25° C.±2° C./60% RH±5% and were analyzed at initial, after 2 weeks, and 1, 2 and 3 months. The analyses were performed in duplicate, with one analysis performed on one vial. Average result of analysis of two vials is reported. Results for formulation of Table 7 are shown in Table 9, and results for formulation of Table 8 are shown in Table 10.

TABLE 9

Stability Tranexamic acid RTU 5 mg/mL
Tranexamic acid RTU 5 mg/ml

| test | Analytical method | Acceptance criteria | Initial | 2 weeks | 1 month | 2 months | 3 months |
|---|---|---|---|---|---|---|---|
| Completeness of solution and visible particles | USP <641> | Clear solution | Cp* | Cp | Cp | Cp | Cp |
| Visible particles | USP <790> | Absence | Cp | Cp | Cp | Cp | Cp |
| Color of the solution | Visual | Colorless | Cp | Cp | Cp | Cp | Cp |
| pH | USP <791> | 6.0-8.0 | 7.25 | 7.24 | 7.23 | 7.24 | 7.23 |
| Assay Tranexamic acid by HPLC | USP <621> | 95.0-105.0% | 99.9% | 100.1% | 99.8% | 99.9% | 100.1% |
| Impurities by HPLC | USP <621> | | | | | | |
| Impurity A | | <0.1% | 0.0 | 0.0 | 0.0 | 0.0 | 0.0 |
| Impurity B | | <0.2% | 0.0 | 0.0 | 0.0 | 0.0 | 0.0 |
| Impurity C | | <0.1% | 0.0 | 0.0 | 0.0 | 0.0 | 0.0 |
| Impurity D | | <0.1% | 0.0 | 0.0 | 0.0 | 0.0 | 0.0 |

TABLE 9-continued

Stability Tranexamic acid RTU 5 mg/mL
Tranexamic acid RTU 5 mg/ml

| test | Analytical method | Acceptance criteria | Initial | 2 weeks | 1 month | 2 months | 3 months |
|---|---|---|---|---|---|---|---|
| Any other impurity | | <0.1% | 0.0 | 0.0 | 0.0 | 0.0 | 0.0 |
| Total impurities | | <0.4% | 0.0 | 0.0 | 0.0 | 0.0 | 0.0 |

*Cp = complies

TABLE 10

Stability Tranexamic acid RTU
Tranexamic acid RTU 10 mg/ml

| test | Analytical method | Acceptance criteria | Initial | 2 weeks | 1 month | 2 months | 3 months |
|---|---|---|---|---|---|---|---|
| Completeness of solution and visible particles | USP <641> | Clear solution | Cp* | Cp | Cp | Cp | Cp |
| Visible particles | USP <790> | Absence | Cp | Cp | Cp | Cp | Cp |
| Color of the solution | Visual | Colorless | Cp | Cp | Cp | Cp | Cp |
| pH | USP <791> | 6.0-8.0 | 7.32 | 7.33 | 7.33 | 7.28 | 7.30 |
| Assay Tranexamic acid by HPLC | USP <621> | 95.0-105.0% | 100.2% | 99.8% | 99.9% | 100.1% | 100.0% |
| Impurities by HPLC | USP <621> | | | | | | |
| Impurity A | | <0.1% | 0.0 | 0.0 | 0.0 | 0.0 | 0.0 |
| Impurity B | | <0.2% | 0.0 | 0.0 | 0.0 | 0.0 | 0.0 |
| Impurity C | | <0.1% | 0.0 | 0.0 | 0.0 | 0.0 | 0.0 |
| Impurity D | | <0.1% | 0.0 | 0.0 | 0.0 | 0.0 | 0.0 |
| Any other impurity | | <0.1% | 0.0 | 0.0 | 0.0 | 0.0 | 0.0 |
| Total impurities | | <0.4% | 0.0 | 0.0 | 0.0 | 0.0 | 0.0 |

*Cp = complies

CONCLUSION

All results were found to be within the acceptance criteria without significant variation. No changes in physicochemical parameters are observed. No impurities are observed. No significant change in the pH is observed. Developed formulations were found to be suitable as per the present experimental preliminary stability data.

Stability studies are performed on validation batches using specifications of Table 1B and analytical procedures of 1A, as described herein for the finished product. Stability studies are carried out at 25° C.±2° C./60% RH±5%: 48 months; 30° C.±2° C./75% RH±5%: 48 months and/or 40° C.±2° C./75% RH±5%: 48 months.

Example 4. Characterization of Water for Injection

The European Pharmacopoeia (Ph Eur) contains standards for grades of water for pharmaceutical use including Water for Injections (WFI). Water for Injections (WFI) is water for the preparation of medicines for parenteral administration when water is used as a vehicle and for dissolving or diluting substances or preparations for parenteral administration before use. One issue is ensuring consistent microbiological quality with respect to removal of bacteria and bacterial endotoxins, for example, by distillation. WFI complies with the tests for Purified Water with additional requirements for bacterial endotoxins of not more than (nmt) 0.25 IU of endotoxin per ml). The WFI bioburden limit is nmt 10 cfu/100 mL, conductivity is 0.6 to 1.5 μS/cm and Total Organic Carbon nmt 0.5 mg/L (=500 ppb). European Monograph for Water for Injections is Ph. Eur. 0169, monograph for Purified Water is Ph. Eur. 0008, monograph for Highly Purified Water is Ph. Eur. 1927. Three lots of WFI was tested by the methods of Table 11A with results as shown in Table 11B.

TABLE 11A

Specifications for Water for Injection

| Test parameter | Method | Specifications |
|---|---|---|
| Total Organic Carbon (TOC) | USP <643> | ≤0.5 mg/L |
| Conductivity | USP <645> | ≤1.5 μS/cm* |
| Bacterial endotoxins | USP <85> | <0.25 EU/mL |
| Total microbial load | USP <61> | <10 cfu/100 mL |

*in house specifications

TABLE 11B

Water for Injection Analysis

| Controls | Specifications | Lot 1 | Lot 2 | Lot 3 |
|---|---|---|---|---|
| Appearance* | Clear and Colorless | Clear and colorless | Clear and colorless | Clear and colorless |
| Nitrates* | <0.2 ppm | <0.2 | <0.2 | <0.2 |
| TOC** | <500 ppb by | 128 | 13.0 | 38 |
| Conductivity at 25° C.** | <2.10 µS/cm | 0.68 | 1.36 | 1.12 |
| Heavy metals* | <0.1 ppm | <0.1 | <0.1 | <0.1 |
| L.A.L. test | <0.06 EU/ml | <0.06 | <0.06 | <0.06 |
| Microbial load* | <10 cfu/100 ml | 0 | 0 | 0 |

*Ph. Eur. Specifications;
**USP Specifications

The WFI used in the compositions of the disclosure had conductivity range from 0.68 to 1.36 µS/cm, with average conductivity at 25° C. of 1.05 µS/cm±0.34 standard deviation. The WFI used in the compositions of the disclosure had TOC range from 13.0 to 128 ppb, with an average TOC of 60 ppb±60 standard deviation.

Example 5. pH Stability of Tranexamic Acid at 5 mg/ml and 10 mg/ml in Sodium Chloride A study of optimal pH for the stability of Tranexamic acid RTU 5 mg/ml and 10 mg/ml in sodium chloride solution was performed. Formulations of Tranexamic acid at 5 mg/ml and 10 mg/ml in sodium chloride were prepared as shown in Example 3 except the initial pH was adjusted to pH 4.0, 5.0, 6.0, 6.5, 7.0, 7.4, 7.8, 8.0, 9.0 and 11.0 using pH adjusters hydrochloric acid or sodium hydroxide. The solutions were stored at either 25° C.=25° C.+2° C./60% RH±5% or 40° C.=40° C.+2° C./75% RH±5%. The solutions were characterized at initial time, after one, two, three, four, five or six months at each storage condition, by the methods shown in Table 12A for completeness of solution, visible particles, and color of the solution.

TABLE 12A pH Stability Assays

| Test | Specification | Method reference |
|---|---|---|
| Completeness of the Solution | Clear solution | USP<641> |
| Visible particles | Absence | USP<790> |
| Color of the solution | Colorless | Ph Eur 2.2.2 |

Results of assays for completeness of solution, visible particles, and color of the solution are shown in Tables 12B to 12E, where C=complies.

TABLE 12B

Tranexamic acid 5 mg/ml

| Batch | pH | Initial | One month 25° C. | One month 40° C. | Two Months 25° C. | Two Months 40° C. | Three Months 25° C. | Three Months 40° C. |
|---|---|---|---|---|---|---|---|---|
| 1 | 4.0 | C | C | C | C | C | C | C |
| 2 | 5.0 | C | C | C | C | C | C | C |
| 3 | 6.0 | C | C | C | C | C | C | C |
| 4 | 6.5 | C | C | C | C | C | C | C |
| 5 | 7.0 | C | C | C | C | C | C | C |
| 6 | 7.4 | C | C | C | C | C | C | C |
| 7 | 8.0 | C | C | C | C | C | C | C |

TABLE 12B-continued

Tranexamic acid 5 mg/ml

| Batch | pH | Initial | One month 25° C. | One month 40° C. | Two Months 25° C. | Two Months 40° C. | Three Months 25° C. | Three Months 40° C. |
|---|---|---|---|---|---|---|---|---|
| 8 | 8.5 | C | C | C | C | C | C | C |
| 9 | 9.0 | C | C | C | C | C | C | C |
| 10 | 11.0 | C | C | C | C | C | C | C |

TABLE 12C

Tranexamic acid 5 mg/ml

| Batch | pH | Four months 25° C. | Four months 40° C. | Five months 25° C. | Five months 40° C. | Six months 25° C. | Six months 40° C. |
|---|---|---|---|---|---|---|---|
| 1 | 4.0 | C | C | C | C | C | C |
| 2 | 5.0 | C | C | C | C | C | C |
| 3 | 6.0 | C | C | C | C | C | C |
| 4 | 6.5 | C | C | C | C | C | C |
| 5 | 7.0 | C | C | C | C | C | C |
| 6 | 7.4 | C | C | C | C | C | C |
| 7 | 7.8 | C | C | C | C | C | C |
| 8 | 8.0 | C | C | C | C | C | C |
| 9 | 9.0 | C | C | C | C | C | C |
| 10 | 11.0 | C | C | C | C | C | C |

TABLE 12D

Tranexamic acid 10 mg/mL

| Batch | pH | Initial | One month 25° C. | One month 40° C. | Two Months 25° C. | Two Months 40° C. | Three Months 25° C. | Three Months 40° C. |
|---|---|---|---|---|---|---|---|---|
| 1 | 4.0 | C | C | C | C | C | C | C |
| 2 | 5.0 | C | C | C | C | C | C | C |
| 3 | 6.0 | C | C | C | C | C | C | C |
| 4 | 6.5 | C | C | C | C | C | C | C |
| 5 | 7.0 | C | C | C | C | C | C | C |
| 6 | 7.4 | C | C | C | C | C | C | C |
| 7 | 8.0 | C | C | C | C | C | C | C |
| 8 | 8.5 | C | C | C | C | C | C | C |
| 9 | 9.0 | C | C | C | C | C | C | C |
| 10 | 11.0 | C | C | C | C | C | C | C |

TABLE 12E 6 month Tranexamic acid 10 mg/mL

| Batch | pH | Four months 25° C. | Four months 40° C. | Five months 25° C. | Five months 40° C. | Six months 25° C. | Six months 40° C. |
|---|---|---|---|---|---|---|---|
| 1 | 4.0 | C | C | C | C | C | C |
| 2 | 5.0 | C | C | C | C | C | C |
| 3 | 6.0 | C | C | C | C | C | C |
| 4 | 6.5 | C | C | C | C | C | C |
| 5 | 7.0 | C | C | C | C | C | C |
| 6 | 7.4 | C | C | C | C | C | C |
| 7 | 7.8 | C | C | C | C | C | C |
| 8 | 8.0 | C | C | C | C | C | C |
| 9 | 9.0 | C | C | C | C | C | C |
| 10 | 11.0 | C | C | C | C | C | C |

Surprisingly, each tranexamic acid composition at 5 mg/ml or 10 mg/ml from pH 4 to pH 11 complied with requirements for completeness of solution, visible particles, and color of the solution when stored for 6 months at 25° C.=25° C.+2° C./60% RH+5% or 40° C.=40° C.+2° C./75% RH+5%.

Test for Particulate Matter

The pH solutions were also evaluated for particulate matter. In this test tranexamic acid solutions at 5 and 10 mg/mL were prepared and adjusted to initial pH 4.0, 5.0, 6.0, 6.5, 7.0, 7.4, 7.8, 8.0, 9.0 or 11.0 in aqueous sodium chloride and stored under two different conditions; either 25° C.=25° C.+2° C./60% RH+5% or 40° C.=40° C.+2° C./75% RH+5%. The solutions were characterized at initial time, after one, three, four, five and six months, by the method shown in Table 13A for Particulate matter under USP<788>. Results are shown in Tables 13B to 13E. Both the Tranexamic acid RTU 5 mg/ml and 10 mg/ml solutions were within specification for particulate matter under USP<788> after 6 months at each pH from 4.0 to 11.0 at 25° C.±2° C./60% RH±5% and/or 40° C.±2° C./75% RH±5%.

TABLE 13A

| Test for Particulate Matter | | |
|---|---|---|
| Test | Specification | Method Reference |
| Particulate Matter | >10 μm: 3000/unit<br>>25 μm: 300/unit | USP <788> |

Results of evaluation for particulate matter are shown in Tables 13B and 13C.

TABLE 13B 3 month pH Stability of Tranexamic acid 5 mg/mL - Particulate Matter

| | | | One month | | Two Months | | Three Months | |
|---|---|---|---|---|---|---|---|---|
| Batch | pH | Initial | 25° C. | 40° C. | 25° C. | 40° C. | 25° C. | 40° C. |
| 1 | 4.0 | 288 | 211 | 245 | / | / | 199 | 183 |
| 2 | 5.0 | 201 | 178 | 204 | / | / | 180 | 193 |
| 3 | 6.0 | 176 | 220 | 193 | / | / | 164 | 169 |
| 4 | 6.5 | 155 | 143 | 189 | / | / | 188 | 138 |
| 5 | 7.0 | 204 | 177 | 188 | / | / | 209 | 144 |
| 6 | 7.4 | 143 | 201 | 164 | / | / | 167 | 172 |
| 7 | 7.8 | 212 | 139 | 200 | / | / | 173 | 162 |
| 8 | 8.0 | 138 | 203 | 124 | / | / | 148 | 167 |
| 9 | 9.0 | 191 | 128 | 167 | / | / | 155 | 182 |
| 10 | 11.0 | 189 | 111 | 202 | / | / | 177 | 191 |

TABLE 13C 6 month pH Stability of Tranexamic acid 5 mg/mL - Particulate Matter

| | | Four months | | Five months | | Six months | |
|---|---|---|---|---|---|---|---|
| Batch | pH | 25° C. | 40° C. | 25° C. | 40° C. | 25° C. | 40° C. |
| 1 | 4.0 | 201 | 203 | 202 | 199 | 184 | 198 |
| 2 | 5.0 | 202 | 199 | 201 | 182 | 178 | 150 |
| 3 | 6.0 | 198 | 205 | 154 | 188 | 149 | 171 |
| 4 | 6.5 | 128 | 153 | 178 | 128 | 180 | 146 |
| 5 | 7.0 | 178 | 149 | 159 | 163 | 179 | 144 |
| 6 | 7.4 | 191 | 202 | 182 | 155 | 201 | 128 |
| 7 | 7.8 | 184 | 158 | 189 | 200 | 195 | 206 |
| 8 | 8.0 | 200 | 156 | 179 | 165 | 139 | 144 |
| 9 | 9.0 | 115 | 123 | 166 | 178 | 161 | 181 |
| 10 | 11.0 | 115 | 149 | 184 | 195 | 124 | 138 |

TABLE 13D 3 month pH Stability of Tranexamic acid 10 mg/mL - Particulate Matter

| | | | One month | | Two Months | | Three Months | |
|---|---|---|---|---|---|---|---|---|
| Batch | pH | Initial | 25° C. | 40° C. | 25° C. | 40° C. | 25° C. | 40° C. |
| 1 | 4.0 | 188 | 203 | 170 | / | / | 142 | 155 |
| 2 | 5.0 | 154 | 189 | 199 | / | / | 202 | 159 |
| 3 | 6.0 | 213 | 220 | 193 | / | / | 161 | 209 |
| 4 | 6.5 | 211 | 143 | 189 | / | / | 179 | 157 |
| 5 | 7.0 | 167 | 177 | 188 | / | / | 154 | 192 |
| 6 | 7.4 | 214 | 201 | 164 | / | / | 188 | 154 |
| 7 | 7.8 | 217 | 139 | 200 | / | / | 190 | 147 |
| 8 | 8.0 | 143 | 203 | 124 | / | / | 169 | 166 |
| 9 | 9.0 | 149 | 128 | 167 | / | / | 183 | 170 |
| 10 | 11.0 | 161 | 111 | 202 | / | / | 137 | 160 |

TABLE 13E 6 month pH Stability of Tranexamic acid 10 mg/mL - Particulate Matter

| | | Four months | | Five months | | Six months | |
|---|---|---|---|---|---|---|---|
| Batch | pH | 25° C. | 40° C. | 25° C. | 40° C. | 25° C. | 40° C. |
| 1 | 4.0 | 144 | 132 | 181 | 151 | 161 | 174 |
| 2 | 5.0 | 187 | 191 | 162 | 180 | 174 | 128 |
| 3 | 6.0 | 203 | 185 | 171 | 153 | 158 | 180 |
| 4 | 6.5 | 184 | 149 | 139 | 172 | 139 | 164 |
| 5 | 7.0 | 174 | 111 | 182 | 193 | 148 | 190 |
| 6 | 7.4 | 202 | 153 | 174 | 168 | 128 | 148 |
| 7 | 7.8 | 169 | 181 | 191 | 166 | 188 | 181 |
| 8 | 8.0 | 159 | 139 | 152 | 124 | 172 | 190 |
| 9 | 9.0 | 139 | 148 | 169 | 177 | 131 | 161 |
| 10 | 11.0 | 202 | 158 | 102 | 171 | 182 | 154 |

A study of optimal pH for the stability of Tranexamic acid RTU 5 mg/ml and 10 mg/ml in sodium chloride solution was performed. Formulations of Tranexamic acid at 5 mg/ml and 10 mg/ml in sodium chloride were prepared as shown in Example 3 except the initial pH was adjusted to pH 4.0, 5.0, 6.0, 6.5, 7.0, 7.4, 7.8, 8.0, 9.0 and 11.0 using pH adjusters hydrochloric acid or sodium hydroxide. The solutions were stored at either 25° C.=25° C.±2° C./60% RH±5% or 40° C.=40° C.±2° C./75% RH±5%. The solutions were characterized at initial time, after one, two, three, four, five and six months, the method shown in Table 14A for pH. Results are shown in Tables 14B to 14E.

TABLE 14A pH Stability Test

| Test | Specification | Method reference |
|---|---|---|
| pH | Variation ±0.5 pH unit | USP<791> |

TABLE 14B pH Stability Tranexamic acid 5 mg/mL in aqueous Sodium Chloride

| | | | One month | | Two Months | | Three Months | |
|---|---|---|---|---|---|---|---|---|
| Batch | pH | Initial | 25° C. | 40° C. | 25° C. | 40° C. | 25° C. | 40° C. |
| 1 | 4.0 | 4.0 | 4.0 | 4.0 | 4.0 | 4.0 | 4.0 | 4.0 |
| 2 | 5.0 | 5.0 | 5.0 | 5.0 | 5.0 | 5.0 | 5.0 | 5.0 |
| 3 | 6.0 | 6.0 | 6.0 | 6.0 | 6.0 | 6.0 | 6.0 | 6.0 |
| 4 | 6.5 | 6.5 | 6.5 | 6.5 | 6.5 | 6.5 | 6.5 | 6.5 |
| 5 | 7.0 | 7.0 | 7.0 | 7.0 | 7.0 | 7.0 | 7.0 | 7.0 |
| 6 | 7.4 | 7.4 | 7.3 | 7.4 | 7.4 | 7.4 | 7.5 | 7.5 |
| 7 | 7.8 | 7.8 | 7.7 | 7.7 | 7.8 | 7.7 | 7.7 | 7.8 |
| 8 | 8.0 | 7.9 | 7.8 | 7.9 | 8.0 | 8.0 | 7.8 | 8.0 |
| 9 | 9.0 | 9.0 | 8.9 | 8.9 | 9.0 | 8.9 | 8.9 | 8.9 |
| 10 | 11.0 | 11.0 | 10.8 | 10.9 | 10.9 | 11.1 | 10.9 | 10.8 |

TABLE 14C 6 month pH Stability Tranexamic acid 5 mg/mL in aqueous Sodium Chloride

| | | Four months | | Five months | | Six months | |
|---|---|---|---|---|---|---|---|
| Batch | pH | 25° C. | 40° C. | 25° C. | 40° C. | 25° C. | 40° C. |
| 1 | 4.0 | 4.0 | 4.1 | 4.0 | 4.1 | 4.0 | 4.0 |
| 2 | 5.0 | 5.1 | 5.0 | 5.0 | 5.1 | 5.0 | 5.0 |
| 3 | 6.0 | 6.0 | 6.0 | 6.1 | 6.0 | 6.0 | 6.0 |
| 4 | 6.5 | 6.5 | 6.5 | 6.5 | 6.5 | 6.5 | 6.5 |
| 5 | 7.0 | 7.0 | 7.0 | 7.0 | 7.1 | 7.1 | 7.0 |
| 6 | 7.4 | 7.5 | 7.4 | 7.5 | 7.5 | 7.6 | 7.5 |
| 7 | 7.8 | 7.7 | 7.8 | 7.9 | 7.8 | 7.9 | 7.8 |
| 8 | 8.0 | 8.1 | 8.0 | 8.1 | 8.1 | 8.0 | 8.0 |
| 9 | 9.0 | 9.0 | 9.0 | 9.0 | 9.0 | 8.9 | 8.9 |
| 10 | 11.0 | 10.9 | 11.0 | 10.9 | 11.1 | 10.9 | 10.9 |

TABLE 14D pH Stability Tranexamic acid 10 mg/mL in aqueous Sodium Chloride

| | | | One month | | Two Months | | Three Months | |
|---|---|---|---|---|---|---|---|---|
| Batch | pH | Initial | 25° C. | 40° C. | 25° C. | 40° C. | 25° C. | 40° C. |
| 1 | 4.0 | 4.0 | 4.0 | 4.0 | 4.0 | 4.1 | 4.0 | 4.0 |
| 2 | 5.0 | 5.0 | 5.0 | 5.0 | 5.1 | 5.0 | 5.0 | 5.0 |
| 3 | 6.0 | 6.0 | 6.0 | 6.0 | 6.0 | 6.0 | 6.0 | 6.0 |
| 4 | 6.5 | 6.5 | 6.5 | 6.5 | 6.5 | 6.5 | 6.5 | 6.5 |
| 5 | 7.0 | 7.0 | 7.0 | 7.0 | 7.0 | 7.2 | 7.1 | 7.0 |
| 6 | 7.4 | 7.4 | 7.4 | 7.5 | 7.5 | 7.4 | 7.4 | 7.4 |

TABLE 14D-continued pH Stability Tranexamic acid 10 mg/mL in aqueous Sodium Chloride

| Batch | pH | Initial | One month 25° C. | One month 40° C. | Two Months 25° C. | Two Months 40° C. | Three Months 25° C. | Three Months 40° C. |
|---|---|---|---|---|---|---|---|---|
| 7 | 7.8 | 7.8 | 7.7 | 7.8 | 7.6 | 7.9 | 7.7 | 7.8 |
| 8 | 8.0 | 8.0 | 7.9 | 7.9 | 8.1 | 8.0 | 7.9 | 8.0 |
| 9 | 9.0 | 9.0 | 8.9 | 8.9 | 8.9 | 9.0 | 8.9 | 8.9 |
| 10 | 11.0 | 11.0 | 10.9 | 10.9 | 11.1 | 11.1 | 10.8 | |

TABLE 14E 6 month pH Stability Tranexamic acid 10 mg/mL in aqueous Sodium Chloride

| Batch | pH | Four months 25° C. | Four months 40° C. | Five months 25° C. | Five months 40° C. | Six months 25° C. | Six months 40° C. |
|---|---|---|---|---|---|---|---|
| 1 | 4.0 | 4.0 | 4.0 | 4.1 | 4.1 | 4.0 | 4.0 |
| 2 | 5.0 | 5.1 | 5.0 | 5.0 | 5.1 | 5.0 | 5.0 |
| 3 | 6.0 | 6.0 | 6.0 | 6.1 | 6.0 | 6.0 | 6.0 |
| 4 | 6.5 | 6.5 | 6.4 | 6.4 | 6.5 | 6.5 | 6.5 |
| 5 | 7.0 | 6.9 | 7.0 | 6.9 | 7.1 | 7.0 | 7.0 |
| 6 | 7.4 | 7.5 | 7.4 | 7.5 | 7.4 | 7.4 | 7.4 |
| 7 | 7.8 | 7.8 | 7.8 | 7.7 | 7.6 | 7.8 | 7.9 |
| 8 | 8.0 | 8.0 | 8.1 | 7.9 | 8.1 | 8.0 | 8.0 |
| 9 | 9.0 | 9.1 | 8.8 | 8.9 | 9.0 | 8.9 | 8.9 |
| 10 | 11.0 | 11.1 | 11.1 | 10.9 | 11.0 | 10.9 | 10.9 |

The pH stability samples were evaluated by HPLC for tranexamic acid content at baseline, one, two, three, four, five and six months after storage at 25° C.=25° C.±2° C./60% RH±5% or 40° C.=40° C.±2° C./75% RH±5% by the method of Table 15A. Results are shown in Tables 15B to 15E for tranexamic acid at 5 mg/mL or 10 mg/mL in aqueous sodium chloride prepared as shown in Example 3 at the indicated pH value.

TABLE 15A

HPLC Assay for Tranexamic Acid

| Test | Specification | Method reference |
|---|---|---|
| Assay (HPLC content) | 95.0-105.5% | HPLC USP<621> |

TABLE 15B pH Stability Tranexamic acid 5 mg/mL in aqueous Sodium Chloride - Tranexamic acid content, HPLC %

| Batch | pH | Initial | One month 25° C. | One month 40° C. | Two Months 25° C. | Two Months 40° C. | Three Months 25° C. | Three Months 40° C. |
|---|---|---|---|---|---|---|---|---|
| 1 | 4.0 | 99.9% | 99.7% | 99.9% | 100.0% | 100.2% | 100.1% | 99.8% |
| 2 | 5.0 | 100.2% | 99.7% | 99.6% | 99.9% | 100.0% | 99.9% | 99.9% |
| 3 | 6.0 | 100.4% | 100.3% | 100.1% | 99.9% | 99.8% | 100.2% | 99.9% |
| 4 | 6.5 | 99.6% | 99.8% | 100.1% | 100.2% | 100.1% | 100.0% | 100.3% |
| 5 | 7.0 | 100.5% | 100.0% | 99.8% | 99.8% | 99.7% | 100.2% | 99.6% |
| 6 | 7.4 | 100.5% | 100.4% | 99.3% | 99.8% | 99.9% | 100.2% | 100.1% |
| 7 | 7.8 | 100.1% | 99.8% | 100.3% | 100.2% | 100.2% | 100.9% | 100.0% |
| 8 | 8.0 | 100.5% | 99.6% | 99.5% | 100.1% | 100.0% | 100.2% | 100.2% |
| 9 | 9.0 | 100.2% | 100.6% | 99.9% | 99.8% | 100.1% | 100.7% | 100.2% |
| 10 | 11.0 | 100.4% | 100.6% | 100.0% | 99.9% | 99.9% | 100.3% | 100.5% |

TABLE 15C 6 month pH Stability Tranexamic acid 5 mg/mL in aqueous Sodium Chloride -Tranexamic acid content, HPLC %

| Batch | pH | Four months 25° C. | Four months 40° C. | Five months 25° C. | Five months 40° C. | Six months 25° C. | Six months 40° C. |
|---|---|---|---|---|---|---|---|
| 1 | 4.0 | 99.9% | 99.8% | 100.0% | 99.9% | 99.8% | 99.8% |
| 2 | 5.0 | 100.1% | 99.8% | 99.8% | 99.9% | 99.7% | 100.2% |
| 3 | 6.0 | 99.8% | 99.9% | 100.1% | 99.8% | 99.7% | 100.2% |
| 4 | 6.5 | 99.9% | 100.0% | 99.8% | 100.1% | 100.1% | 99.8% |
| 5 | 7.0 | 100.1% | 99.9% | 100.1% | 100.0% | 99.9% | 100.4% |
| 6 | 7.4 | 99.9% | 99.8% | 100.3% | 100.1% | 100.3% | 100.5% |
| 7 | 7.8 | 99.9% | 100.0% | 99.8% | 99.9% | 100.4% | 100.1% |
| 8 | 8.0 | 100.2% | 99.9% | 99.9% | 99.8% | 100.1% | 100.3% |
| 9 | 9.0 | 100.2% | 100.3% | 100.2% | 100.1% | 100.9% | 100.4% |
| 10 | 11.0 | 100.4% | 100.1% | 100.3% | 100.1% | 100.2% | 100.4% |

TABLE 15D pH Stability Tranexamic acid 10 mg/mL in aqueous
Sodium Chloride - Tranexamic acid content HPLC %

| Batch | pH | Initial | One month | | Two Months | | Three Months | |
|---|---|---|---|---|---|---|---|---|
| | | | 25° C. | 40° C. | 25° C. | 40° C. | 25° C. | 40° C. |
| 1 | 4.0 | 99.7% | 99.2% | 99.8% | 99.8% | 99.6% | 99.5% | 99.2% |
| 2 | 5.0 | 99.8% | 98.9% | 100.1% | 100.2% | 100.0% | 99.6% | 99.4% |
| 3 | 6.0 | 100.7% | 99.5% | 100.2% | 99.6% | 99.8% | 99.8% | 99.1% |
| 4 | 6.5 | 100.4% | 100.2% | 99.9% | 99.8% | 100.1% | 99.9% | 99.6% |
| 5 | 7.0 | 100.4% | 99.8% | 99.7% | 100.2% | 100.1% | 100.2% | 99.7% |
| 6 | 7.4 | 101.1% | 101.1% | 99.5% | 99.9% | 99.9% | 100.5% | 99.7% |
| 7 | 7.8 | 101.4% | 100.2% | 100.8% | 99.8% | 100.1% | 100.8% | 100.1% |
| 8 | 8.0 | 101.2% | 99.5% | 99.2% | 100.2% | 99.8% | 100.7% | 100.6% |
| 9 | 9.0 | 101.6% | 100.5% | 100.8% | 99.8% | 100.1% | 100.6% | 100.2% |
| 10 | 11.0 | 102.1% | 100.7% | 100.2% | 100.0% | 99.8% | 101.1% | 100.8% |

TABLE 15E 6 month pH Stability Tranexamic acid 10 mg/mL in aqueous
Sodium Chloride -Tranexamic acid content HPLC %

| Batch | pH | Four months | | Five months | | Six months | |
|---|---|---|---|---|---|---|---|
| | | 25° C. | 40° C. | 25° C. | 40° C. | 25° C. | 40° C. |
| 1 | 4.0 | 100.1% | 100.2% | 99.6% | 99.8% | 99.4% | 99.5% |
| 2 | 5.0 | 99.9% | 100.0% | 99.9% | 99.7% | 100.2% | 99.5% |
| 3 | 6.0 | 99.9% | 99.8% | 99.8% | 99.8% | 99.6% | 99.9% |
| 4 | 6.5 | 100.1% | 99.8% | 99.9% | 100.0% | 100.0% | 99.8% |
| 5 | 7.0 | 99.9% | 99.9% | 99.7% | 99.8% | 99.9% | 99.9% |
| 6 | 7.4 | 100.0% | 99.8% | 100.1% | 100.2% | 100.5% | 100.4% |
| 7 | 7.8 | 99.8% | 99.8% | 99.9% | 99.9% | 100.4% | 100.5% |
| 8 | 8.0 | 99.9% | 100.1% | 99.8% | 100.3% | 100.1% | 100.4% |
| 9 | 9.0 | 100.1% | 100.2% | 100.2% | 100.4% | 100.2% | 100.2% |
| 10 | 11.0 | 100.1% | 100.3% | 99.9% | 100.1% | 100.4% | 100.5% |

Each Tranexamic acid 5 mg/mL and 10 mg/mL ready to use solution in aqueous sodium chloride from pH 4.0 to pH 11.0 remained stable and exhibited greater than 97% of undegraded tranexamic acid compared to initial concentration when stored for at least 6 months at 25° C.±2° C./60% RH±5% or 40° C.=40° C.±2° C./75% RH±5%.

Each Tranexamic acid 5 mg/mL and 10 mg/mL ready to use solution in aqueous sodium chloride from pH 6.0 to pH 8.0 remained stable and exhibited greater than 98% of undegraded tranexamic acid compared to initial concentration when stored for at least 6 months at 25° C.±2° C./60% RH±5% or 40° C.=40° C.±2° C./75% RH±5%.

HPLC impurity profiles for each of the pH stability samples were also obtained as shown in Table 15A. HPLC method for assay and impurities was developed with references standards USP Tranexamic Acid RS and USP Tranexamic Acid Related Compound C RS.

Chromatic conditions were: Column: octadecylsilyl (C18) silica gel for chromatography. 25 cm×4.6 mm (5 μm) (column L1 of the USP); Mobile phase: dissolve 11.0 g of anhydrous sodium dihydrogen phosphate in 500 ml of water and add 5 ml of triethylamine and 1.4 g of sodium laurilsulfate. Adjust to pH 2.5 with dilute phosphoric acid and dilute to 600 ml with water. Add 400 ml of methanol and mix. Column temperature: ambient. Flow rate: 0.9 ml/min; Detection: spectrophotometer at 220 nm; Injection volume: 20 μl; Run time: 40 minutes. The Test solution was diluted in water to 0.5 mg/ml. The Standard solution was prepared with USP Tranexamic Acid RS at 0.5 mg/ml in water.

System suitability was performed as follows. Resolution: 0.2 mg/ml of USP Tranexamic Acid RS and 0.002 mg/ml of USP Tranexamic Acid Related Compound C RS in water. Resolution is not less than 2.0 between Tranexamic Acid and Tranexamic Acid Related Compound C.

Asymmetry: Asymmetry of peak of USP Tranexamic Acid RS is maximum 2.0. Precision: Standard deviation of six injections of USP Tranexamic Acid RS is maximum 2.0%. Calculation: Area of Tranexamic acid in the test solution versus the area of USP Tranexamic Acid RS in the standard solution taking into consideration practical weight and declared potency of standard.

Assay of impurities by HPLC utilized same column, mobile phase, column temperature, flow rate, detection, run time as in assay shown above. The injection volume was 90 μl. Test solution, for the tranexamic acid 5 mg/mL the assay was performed without dilution. For the tranexamic acid 10 mg/mL, the sample was diluted in water to 5 mg/mL. The standard solution was prepared with USP Tranexamic Acid RS at 2.5 μg/ml in water. Mobile phase is injected at same injection volume of 90 μl. For System suitability: Resolution: Same as in assay. Asymmetry: Asymmetry of peak of USP Tranexamic Acid RS is maximum 2.5. Precision: Standard deviation of six injections of USP Tranexamic Acid RS is maximum 10.0%.

The following peaks are discarded in the chromatograms of test solutions: peaks that are present in the mobile phase chromatogram are discarded. Disregard limit: 0.05 times the area of the principal peak in the chromatogram obtained with Standard solution for assay of impurities: 0.025 percent (according to the USP). Known impurities A, B, C and D are identified by the relative retention time of the peak of each impurity, when exist in the test solution, in relation with the peak of Tranexamic acid according to Table 16A which corresponds to Impurity Table 1" of the USP:

TABLE 16A

Impurity Table 1

| Name | Relative Retention Time | Relative Response Factor | Acceptance Criteria NMT (%) |
|---|---|---|---|
| Tranexamic acid related compound A[a] | 2.1 | 1 | 0.1 |
| Tranexamic acid related compound B[b] | 1.5 | 1.2 | 0.2 |
| Tranexamic acid related compound C[c] | 1.1 | 0.005 | 0.1 |
| Tranexamic acid | 1.0 | 1.0 | — |

TABLE 16A-continued

Impurity Table 1

| Name | Relative Retention Time | Relative Response Factor | Acceptance Criteria NMT (%) |
|---|---|---|---|
| Tranexamic acid related compound D[d] | 1.3 | 0.006 | 0.1 |

[a]Trans,trans-4,4'-(Iminodimethylene)di(cyclohexanecarboxylic)acid
[b]Cis-4-(Aminomethyl)cyclohexanecarboxylic acid
[c](RS)-4-(Aminomethyl)cyclohex-1-enecarboxylic acid
[d]4-Aminomethyl benzoic acid Reporting limit is 0.05%. This means 0.05% of analysis concentration of test solution. Analysis concentration of test solution is 5 mg/ml, therefore, reporting limit is 2.5 μg/ml. Only results above reporting limit are reported. HPLC impurity limits are shown in Table 16B.

TABLE 16B pH Stability-HPLC Assay of Impurities

| Test | Specification | Method reference |
|---|---|---|
| Assay of impurities | | HPLC<621> |
| Impurity A | ≤0.1% | |
| Impurity B | ≤0.2% | |
| Impurity C | ≤0.1% | |
| Impurity D | ≤0.1% | |
| Any unknown impurity | ≤0.1% | |
| Total | ≤0.4% | |
| Reporting | Reporting limit is 0.05%: Only results that are above 0.05% are reported. Results below 0.05% are reported as BRL: Below Reporting Limit | |

Results of impurities over 6 months of the study are shown in Tables 16C to 16F.

TABLE 16C pH Stability Tranexamic acid 5 mg/mL HPLC Impurities

| pH | Impurities | Initial | One month 25° C. | One month 40° C. | Two Months 25° C. | Two Months 40° C. | Three Months 25° C. | Three Months 40° C. |
|---|---|---|---|---|---|---|---|---|
| 4.0 | A, B, unknown | Absence | Absence | Absence | Absence | Absence | Absence | Absence |
|  | C, D, Total | BRL | BRL | BRL | BRL | BRL | BRL | BRL |
| 5.0 | A, B, unknown | Absence | Absence | Absence | Absence | Absence | Absence | Absence |
|  | C, D, Total | BRL | BRL | BRL | BRL | BRL | BRL | BRL |
| 6.0 | A, B, unknown | Absence | Absence | Absence | Absence | Absence | Absence | Absence |
|  | C, D, Total | BRL | BRL | BRL | BRL | BRL | BRL | BRL |
| 6.5 | A, B, unknown | Absence | Absence | Absence | Absence | Absence | Absence | Absence |
|  | C, D, Total | BRL | BRL | BRL | BRL | BRL | BRL | BRL |
| 7.0 | A, B, unknown | Absence | Absence | Absence | Absence | Absence | Absence | Absence |
|  | C, D, Total | BRL | BRL | BRL | BRL | BRL | BRL | BRL |
| 7.4 | A, B, unknown | Absence | Absence | Absence | Absence | Absence | Absence | Absence |
|  | C, D, Total | BRL | BRL | BRL | BRL | BRL | BRL | BRL |
| 7.8 | A, B, unknown | Absence | Absence | Absence | Absence | Absence | Absence | Absence |
|  | C, D, Total | BRL | BRL | BRL | BRL | BRL | BRL | BRL |
| 8.0 | A, B, unknown | Absence | Absence | Absence | Absence | Absence | Absence | Absence |
|  | C, D, Total | BRL | BRL | BRL | BRL | BRL | BRL | BRL |
| 9.0 | A, B, unknown | Absence | Absence | Absence | Absence | Absence | Absence | Absence |
|  | C, D, Total | BRL | BRL | BRL | BRL | BRL | BRL | BRL |
| 11.0 | A, B, unknown | Absence | Absence | Absence | Absence | Absence | Absence | Absence |
|  | C, D, Total | BRL | BRL | BRL | BRL | BRL | BRL | BRL |

TABLE 16D 6 month pH Stability Tranexamic acid 5 mg/mL HPLC Impurities

| pH | Impurities | Four months 25° C. | Four months 40° C. | Five months 25° C. | Five months 40° C. | Six months 25° C. | Six months 40° C. |
|---|---|---|---|---|---|---|---|
| 4.0 | A, B, unknown | Absence | Absence | Absence | Absence | Absence | Absence |
|  | C, D, Total | BRL | BRL | BRL | BRL | BRL | BRL |
| 5.0 | A, B, unknown | Absence | Absence | Absence | Absence | Absence | Absence |
|  | C, D, Total | BRL | BRL | BRL | BRL | BRL | BRL |
| 6.0 | A, B, unknown | Absence | Absence | Absence | Absence | Absence | Absence |
|  | C, D, Total | BRL | BRL | BRL | BRL | BRL | BRL |
| 6.5 | A, B, unknown | Absence | Absence | Absence | Absence | Absence | Absence |
|  | C, D, Total | BRL | BRL | BRL | BRL | BRL | BRL |
| 7.0 | A, B, unknown | Absence | Absence | Absence | Absence | Absence | Absence |
|  | C, D, Total | BRL | BRL | BRL | BRL | BRL | BRL |
| 7.4 | A, B, unknown | Absence | Absence | Absence | Absence | Absence | Absence |
|  | C, D, Total | BRL | BRL | BRL | BRL | BRL | BRL |
| 7.8 | A, B, unknown | Absence | Absence | Absence | Absence | Absence | Absence |
|  | C, D, Total | BRL | BRL | BRL | BRL | BRL | BRL |
| 8.0 | A, B, unknown | Absence | Absence | Absence | Absence | Absence | Absence |
|  | C, D, Total | BRL | BRL | BRL | BRL | BRL | BRL |
| 9.0 | A, B, unknown | Absence | Absence | Absence | Absence | Absence | Absence |
|  | C, D, Total | BRL | BRL | BRL | BRL | BRL | BRL |

TABLE 16D-continued 6 month pH Stability Tranexamic acid 5 mg/mL HPLC Impurities

| | | Four months | | Five months | | Six months | |
|---|---|---|---|---|---|---|---|
| pH | Impurities | 25° C. | 40° C. | 25° C. | 40° C. | 25° C. | 40° C. |
| 11.0 | A, B, unknown | Absence | Absence | Absence | Absence | Absence | Absence |
| | C, D, Total | BRL | BRL | BRL | BRL | BRL | BRL |

TABLE 16E pH Stability Tranexamic acid 10 mg/mL HPLC Impurities

| | | | One month | | Two Months | | Three Months | |
|---|---|---|---|---|---|---|---|---|
| pH | Impurities | Initial | 25° C. | 40° C. | 25° C. | 40° C. | 25° C. | 40° C. |
| 4.0 | A, B, unknown | Absence | Absence | Absence | Absence | Absence | Absence | Absence |
| | C, D, Total | BRL | BRL | BRL | BRL | BRL | BRL | BRL |
| 5.0 | A, B, unknown | Absence | Absence | Absence | Absence | Absence | Absence | Absence |
| | C, D, Total | BRL | BRL | BRL | BRL | BRL | BRL | BRL |
| 6.0 | A, B, unknown | Absence | Absence | Absence | Absence | Absence | Absence | Absence |
| | C, D, Total | BRL | BRL | BRL | BRL | BRL | BRL | BRL |
| 6.5 | A, B, unknown | Absence | Absence | Absence | Absence | Absence | Absence | Absence |
| | C, D, Total | BRL | BRL | BRL | BRL | BRL | BRL | BRL |
| 7.0 | A, B, unknown | Absence | Absence | Absence | Absence | Absence | Absence | Absence |
| | C, D, Total | BRL | BRL | BRL | BRL | BRL | BRL | BRL |
| 7.4 | A, B, unknown | Absence | Absence | Absence | Absence | Absence | Absence | Absence |
| | C, D, Total | BRL | BRL | BRL | BRL | BRL | BRL | BRL |
| 7.8 | A, B, unknown | Absence | Absence | Absence | Absence | Absence | Absence | Absence |
| | C, D, Total | BRL | BRL | BRL | BRL | BRL | BRL | BRL |
| 8.0 | A, B, unknown | Absence | Absence | Absence | Absence | Absence | Absence | Absence |
| | C, D, Total | BRL | BRL | BRL | BRL | BRL | BRL | BRL |
| 9.0 | A, B, unknown | Absence | Absence | Absence | Absence | Absence | Absence | Absence |
| | C, D, Total | BRL | BRL | BRL | BRL | BRL | BRL | BRL |
| 11.0 | A, B, unknown | Absence | Absence | Absence | Absence | Absence | Absence | Absence |
| | C, D, Total | BRL | BRL | BRL | BRL | BRL | BRL | BRL |

TABLE 16F 6 month pH Stability Tranexamic acid 10 mg/mL HPLC Impurities

| | | Four months | | Five months | | Six months | |
|---|---|---|---|---|---|---|---|
| pH | Impurities | 25° C. | 40° C. | 25° C. | 40° C. | 25° C. | 40° C. |
| 4.0 | A, B, unknown | Absence | Absence | Absence | Absence | Absence | Absence |
| | C, D, Total | BRL | BRL | BRL | BRL | BRL | BRL |
| 5.0 | A, B, unknown | Absence | Absence | Absence | Absence | Absence | Absence |
| | C, D, Total | BRL | BRL | BRL | BRL | BRL | BRL |
| 6.0 | A, B, unknown | Absence | Absence | Absence | Absence | Absence | Absence |
| | C, D, Total | BRL | BRL | BRL | BRL | BRL | BRL |
| 6.5 | A, B, unknown | Absence | Absence | Absence | Absence | Absence | Absence |
| | C, D, Total | BRL | BRL | BRL | BRL | BRL | BRL |
| 7.0 | A, B, unknown | Absence | Absence | Absence | Absence | Absence | Absence |
| | C, D, Total | BRL | BRL | BRL | BRL | BRL | BRL |
| 7.4 | A, B, unknown | Absence | Absence | Absence | Absence | Absence | Absence |
| | C, D, Total | BRL | BRL | BRL | BRL | BRL | BRL |
| 7.8 | A, B, unknown | Absence | Absence | Absence | Absence | Absence | Absence |
| | C, D, Total | BRL | BRL | BRL | BRL | BRL | BRL |
| 8.0 | A, B, unknown | Absence | Absence | Absence | Absence | Absence | Absence |
| | C, D, Total | BRL | BRL | BRL | BRL | BRL | BRL |
| 9.0 | A, B, unknown | Absence | Absence | Absence | Absence | Absence | Absence |
| | C, D, Total | BRL | BRL | BRL | BRL | BRL | BRL |
| 11.0 | A, B, unknown | Absence | Absence | Absence | Absence | Absence | Absence |
| | C, D, Total | BRL | BRL | BRL | BRL | BRL | BRL |

As shown in Tables 16C to 16F, surprisingly for each of the pH values from 4.0 to 11.0 for both 5 mg/mL and 10 mg/mL tranexamic acid in aqueous sodium chloride, impurities A, B, and unknown were not detected, while impurities C, D and total impurities were below reporting limit of Table 16B when stored for at least six months at 25° C.=25° C.±2° C./60% RH±5% or 40° C.=40° C.±2° C./75% RH±5%.

What is claimed is:

1. An aqueous pharmaceutical composition in the form of a solution for parenteral administration comprising: tranexamic acid or a pharmaceutically acceptable salt thereof; and a tonicity agent, wherein the composition requires no dilution before administration and has a pH from 6.0 to 8.0.

2. The aqueous pharmaceutical composition of claim 1, comprising from 0.05 to 15 mg/mL tranexamic acid.

3. The aqueous pharmaceutical composition of claim 1, comprising 5 mg/mL tranexamic acid.

4. The aqueous pharmaceutical composition of claim 1, comprising 10 mg/mL tranexamic acid.

5. The aqueous pharmaceutical composition of claim 1, wherein the tonicity agent is selected from the group consisting of sodium chloride, dextrose, sucrose, xylitol, fructose, glycerol, sorbitol, mannitol, potassium chloride, mannose, calcium chloride, and magnesium chloride.

6. The aqueous pharmaceutical composition of claim 1, comprising the tonicity agent in a concentration effective to impart osmolality of from 270 to 340 mOsm/kg.

7. The aqueous pharmaceutical composition of claim 1, wherein the tonicity agent is sodium chloride.

8. The aqueous pharmaceutical composition of claim 7, comprising from 5 to 10 mg/mL sodium chloride.

9. The aqueous pharmaceutical composition of claim 1, wherein the tonicity agent is mannitol.

10. The aqueous pharmaceutical composition of claim 9, comprising from 35 to 45 mg/mL mannitol.

11. The aqueous pharmaceutical composition of claim 1, wherein the composition maintains at least about 95% of the tranexamic acid in undegraded form after storage for 180 days at 25° C.

12. The aqueous pharmaceutical composition of claim 1, wherein the composition maintains at least about 98% of the tranexamic acid in undegraded form after storage for 180 days at 25° C.

13. The aqueous pharmaceutical composition of claim 1, further comprising at least one pH adjuster selected from the group consisting of hydrochloric acid, sodium hydroxide and a mixture thereof.

14. The aqueous pharmaceutical composition of claim 1, further comprising water for injection having conductivity at 25° C. of 0.6 to 1.5 mS/cm.

15. A pharmaceutical composition for parenteral administration comprising a ready-to-use aqueous solution with a pH from about 6.0 to about 8.0 comprising: from 0.05 to about 15 mg/mL tranexamic acid or a pharmaceutically acceptable salt thereof; a tonicity agent selected from (i) about 35 mg/mL to about 45 mg/mL mannitol or (ii) about 6.8-8.2 mg/mL sodium chloride; and a pH adjuster in an amount to provide initial pH from about 6.0 to about 8.0.

16. The aqueous pharmaceutical composition of claim 15, further comprising water for injection having conductivity at 25° C. of 0.6 to 1.5 mS/cm.

17. The pharmaceutical composition of claim 15, wherein the aqueous solution is contained in a pharmaceutically acceptable container.

18. The pharmaceutical composition of claim 15, wherein the aqueous solution when stored in the container for at least one year at room temperature exhibits (i) less than a 10% decrease in the concentration of tranexamic acid and (ii) a total impurity formation of less than about 3%.

19. The aqueous pharmaceutical composition of claim 15, comprising 5 mg/mL tranexamic acid.

20. The aqueous pharmaceutical composition of claim 15, comprising 10 mg/mL tranexamic acid.

21. A method for reducing or preventing hemorrhage associated with tooth extraction in a patient with coagulopathy comprising steps of:
    (a) administering the composition of claim 1 to the patient immediately before tooth extraction; and
    (b) administering the composition of claim 1 to the patient for 2 to 8 days following tooth extraction.

22. The method of claim 21, wherein step (a) further comprises concomitant administration of replacement therapy.

23. The method of claim 21, wherein step (a) comprises intravenous administration of the composition at a dose of 10 mg tranexamic acid per kg body weight of the patient.

24. The method of claim 21, wherein step (b) comprises intravenous administration of the composition at a dose of 10 mg tranexamic acid per kg body weight of the patient three to four times per day.

* * * * *